(12) United States Patent
Nunan

(10) Patent No.: US 12,256,913 B2
(45) Date of Patent: *Mar. 25, 2025

(54) SURGICAL TOOL INCLUDING AN INELASTIC AND ELASTIC CABLE TO BE TENSIONED TO IMPART A BEND

(71) Applicant: Stryker European Operations Holdings LLC, Kalamazoo, MI (US)

(72) Inventor: Gerard W. Nunan, Ballincollig (IE)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/888,870

(22) Filed: Aug. 16, 2022

(65) Prior Publication Data

US 2022/0387012 A1   Dec. 8, 2022

Related U.S. Application Data

(60) Continuation of application No. 16/587,823, filed on Sep. 30, 2019, now Pat. No. 11,457,902, which is a
(Continued)

(51) Int. Cl.
*A61B 17/00* (2006.01)
*A61B 1/00* (2006.01)
(Continued)

(52) U.S. Cl.
CPC .... *A61B 17/00234* (2013.01); *A61B 1/00078* (2013.01); *A61B 1/0057* (2013.01);
(Continued)

(58) Field of Classification Search
CPC ........ A61B 17/00234; A61B 17/32002; A61B 17/3421; A61B 17/29; A61B 1/00078;
(Continued)

(56) References Cited

U.S. PATENT DOCUMENTS 3,521,620 A   7/1970 Cook
4,641,657 A   2/1987 Ellis
(Continued)

FOREIGN PATENT DOCUMENTS

CN   101677752 A   3/2010
CN   201469245 U   5/2010
(Continued)

OTHER PUBLICATIONS

English language abstract and machine-assisted English translation for CN 201469245 extracted from espacenet.com database on Oct. 17, 2018, 9 pages.
(Continued)

*Primary Examiner* — Michael J Lau
(74) *Attorney, Agent, or Firm* — Howard & Howard Attorneys PLLC

(57) ABSTRACT

A surgical tool including an inelastic and elastic cable to impart a bend to a shaft. A steering assembly is coupled to the shaft and configured to cause longitudinal displacement of the shaft relative to the body to tension the cables to bend the shaft bendable section in a direction of the flexible inelastic cable. The surgical tool may include an active tip with one of the cables being configured to supply energy to the active tip. The surgical tool may be a shaver that includes a shaver shaft having a flexible section configured to be aligned with a shaft bendable section with the motor of the shaver supported on a cradle of a body. The shaft bendable section may be formed by links with the flexible inelastic cable being arcuately spaced apart from tabs within sockets that engage adjacent links.

20 Claims, 19 Drawing Sheets

Related U.S. Application Data continuation of application No. 15/489,132, filed on Apr. 17, 2017, now Pat. No. 10,492,771, which is a division of application No. PCT/US2015/055624, filed on Oct. 15, 2015.

(60) Provisional application No. 62/065,628, filed on Oct. 18, 2014.

(51) Int. Cl.
  *A61B 1/005* (2006.01)
  *A61B 17/32* (2006.01)
  *A61B 17/34* (2006.01)
  *A61B 17/29* (2006.01)
  *A61B 90/50* (2016.01)
  *A61M 25/01* (2006.01)

(52) U.S. Cl.
  CPC .... *A61B 17/32002* (2013.01); *A61B 17/3421* (2013.01); *A61B 1/0055* (2013.01); *A61B 2017/00296* (2013.01); *A61B 2017/00305* (2013.01); *A61B 2017/00314* (2013.01); *A61B 2017/00323* (2013.01); *A61B 2017/00353* (2013.01); *A61B 17/29* (2013.01); *A61B 2090/508* (2016.02); *A61B 2218/001* (2013.01); *A61M 25/0136* (2013.01); *A61M 25/0138* (2013.01); *A61M 25/0147* (2013.01)

(58) Field of Classification Search
  CPC .............. A61B 1/0057; A61B 1/0055; A61B 2090/508; A61B 2017/00296; A61B 2017/00305; A61B 2017/00314; A61B 2017/00323; A61B 2017/00353; A61M 25/0136; A61M 25/0138; A61M 25/0147
  USPC .......................................................... 606/1
  See application file for complete search history.

(56) References Cited

U.S. PATENT DOCUMENTS

| | | | |
|---|---|---|---|
| 5,599,305 A | | 2/1997 | Hermann et al. |
| 5,715,817 A | | 2/1998 | Stevens-Wright et al. |
| 5,851,212 A | | 12/1998 | Zirps et al. |
| 6,264,630 B1 | | 7/2001 | Mickley et al. |
| 6,391,030 B1 | | 5/2002 | Wagner et al. |
| 6,464,711 B1 | | 10/2002 | Emans et al. |
| 6,645,218 B1 | | 11/2003 | Cassidy et al. |
| 6,958,071 B2 | | 10/2005 | Carusillo et al. |
| 7,811,277 B2 | | 10/2010 | Boulais |
| 10,363,103 B2 * | | 7/2019 | Alvarez ............ A61M 25/0136 |
| 10,492,771 B2 | | 12/2019 | Nunan |
| 10,835,112 B2 * | | 11/2020 | Smith ................. A61B 1/0057 |
| 11,457,902 B2 * | | 10/2022 | Nunan ............... A61B 1/00078 |
| 2001/0047164 A1 | | 11/2001 | Teague et al. |
| 2003/0040666 A1 | | 2/2003 | Rutten et al. |
| 2004/0210109 A1 | | 10/2004 | Jaffe et al. |
| 2005/0187537 A1 * | | 8/2005 | Loeb ................ A61B 17/32002 |
| | | | 606/49 |
| 2005/0226682 A1 | | 10/2005 | Chersky et al. |
| 2006/0199999 A1 | | 9/2006 | Ikeda et al. |
| 2008/0051802 A1 | | 2/2008 | Schostek et al. |
| 2008/0097479 A1 | | 4/2008 | Boehlke et al. |
| 2008/0114364 A1 * | | 5/2008 | Goldin .............. A61B 17/1617 |
| | | | 606/170 |
| 2008/0172037 A1 | | 7/2008 | Huang et al. |
| 2008/0188800 A1 | | 8/2008 | Bencini et al. |
| 2008/0287951 A1 | | 11/2008 | Stoneburner et al. |
| 2009/0082776 A1 | | 3/2009 | Cresina |
| 2009/0112214 A1 | | 4/2009 | Philippon et al. |
| 2009/0171151 A1 * | | 7/2009 | Choset ................. A61B 1/0053 |
| | | | 600/114 |
| 2009/0216245 A1 | | 8/2009 | Viola |
| 2009/0281388 A1 | | 11/2009 | Ito |
| 2010/0010298 A1 * | | 1/2010 | Bakos .................... A61B 1/015 |
| | | | 600/114 |
| 2010/0056868 A1 | | 3/2010 | Kitagawa |
| 2010/0152732 A1 | | 6/2010 | Katou |
| 2010/0152751 A1 | | 6/2010 | Meade et al. |
| 2010/0179540 A1 * | | 7/2010 | Marczyk ............ A61B 18/1445 |
| | | | 606/41 |
| 2010/0210906 A1 | | 8/2010 | Wendlandt |
| 2010/0249497 A1 * | | 9/2010 | Peine ................. A61B 17/2909 |
| | | | 600/104 |
| 2011/0004157 A1 | | 1/2011 | Dewaele et al. |
| 2011/0009863 A1 | | 1/2011 | Marczyk et al. |
| 2011/0054507 A1 | | 3/2011 | Batten et al. |
| 2011/0087269 A1 | | 4/2011 | Stokes et al. |
| 2011/0098711 A1 * | | 4/2011 | Batten ................ A61B 17/1617 |
| | | | 606/84 |
| 2011/0184459 A1 | | 7/2011 | Malkowski et al. |
| 2011/0295069 A1 | | 12/2011 | Ouchi |
| 2011/0295242 A1 | | 12/2011 | Spivey et al. |
| 2012/0010629 A1 | | 1/2012 | Mire et al. |
| 2012/0095498 A1 | | 4/2012 | Stefanchik et al. |
| 2012/0109186 A1 | | 5/2012 | Parrott et al. |
| 2012/0110810 A1 | | 5/2012 | Houser et al. |
| 2012/0253324 A1 * | | 10/2012 | Lee ................... A61B 1/00078 |
| | | | 606/1 |
| 2012/0316591 A1 | | 12/2012 | Thorne et al. |
| 2013/0023860 A1 | | 1/2013 | Nagashimada |
| 2013/0041392 A1 | | 2/2013 | Edwards |
| 2013/0182091 A1 | | 7/2013 | Kohno et al. |
| 2013/0199522 A1 | | 8/2013 | Shockley |
| 2013/0217963 A1 | | 8/2013 | Naito et al. |
| 2013/0253271 A1 * | | 9/2013 | Jeong ................... A61B 1/0055 |
| | | | 600/137 |
| 2014/0012288 A1 | | 1/2014 | Darisse et al. |
| 2014/0018617 A1 | | 1/2014 | Kohno |
| 2014/0025046 A1 | | 1/2014 | Williams et al. |
| 2014/0046305 A1 | | 2/2014 | Castro et al. |
| 2014/0058363 A1 | | 2/2014 | Berkelaar |
| 2014/0188091 A1 | | 7/2014 | Vidal et al. |
| 2014/0276932 A1 * | | 9/2014 | Williams ............. A61B 17/072 |
| | | | 606/130 |
| 2014/0303730 A1 | | 10/2014 | McGuire et al. |
| 2017/0215855 A1 | | 8/2017 | Nunan |
| 2017/0296222 A1 | | 10/2017 | Steele |
| 2020/0022690 A1 | | 1/2020 | Nunan |

FOREIGN PATENT DOCUMENTS

| | | | | |
|---|---|---|---|---|
| CN | 103619271 B | * | 7/2019 | ....... A61B 17/00234 |
| EP | 1017323 B9 | | 6/2007 | |
| EP | 3090776 A1 | * | 11/2016 | ......... A61B 1/00078 |
| WO | WO-9622738 A1 | * | 8/1996 | ....... A61B 17/32002 |

OTHER PUBLICATIONS

English language abstract for CN 101677752 extracted from espacenet.com database on Oct. 17, 2018, 1 page.

EPO, ISA Search Report and Written Opinion for PCT/US2015/055624, Dec. 2015.

Stryker, "debrideX Surgical Company Overview", 2014, 1 page.

* cited by examiner

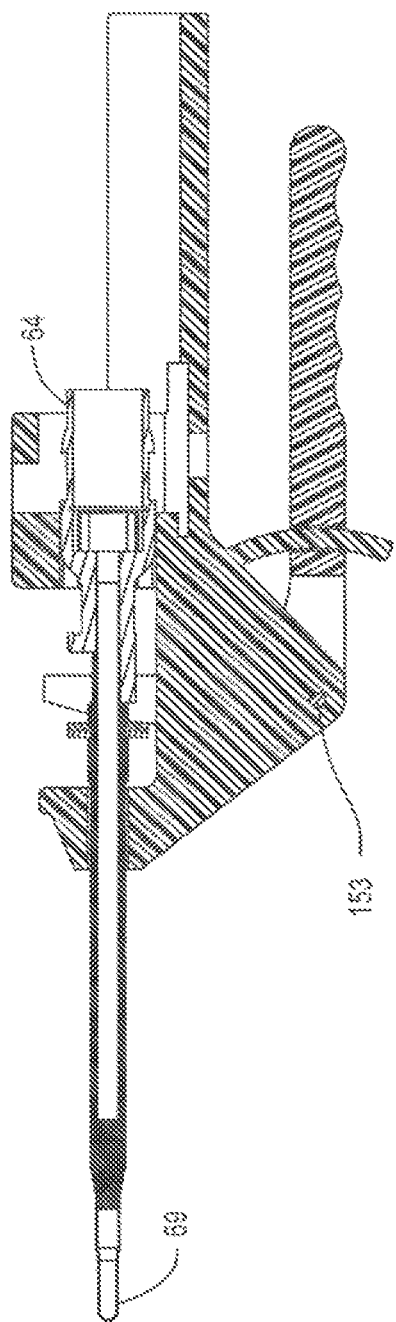

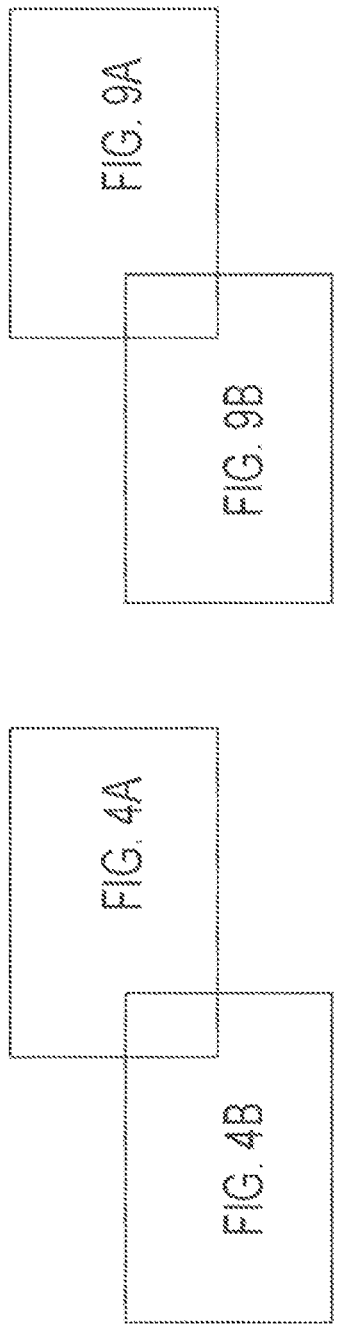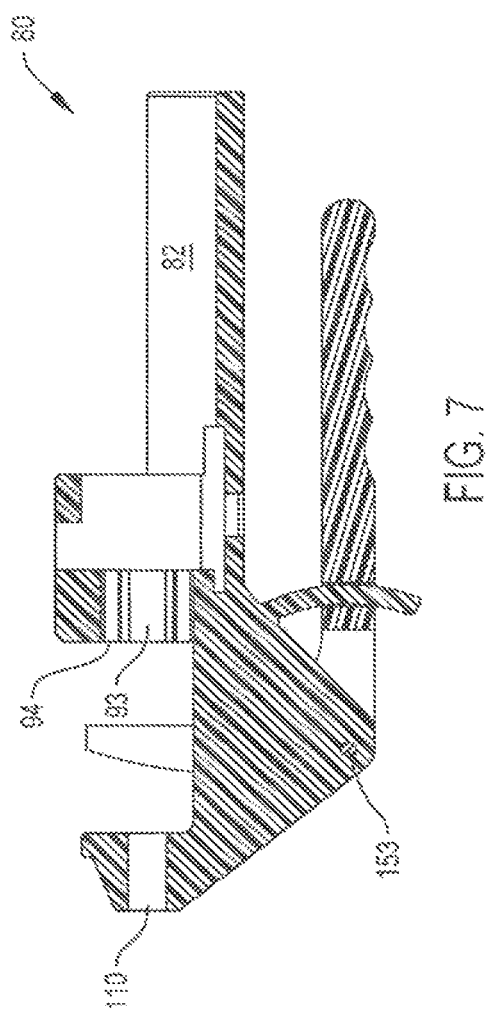

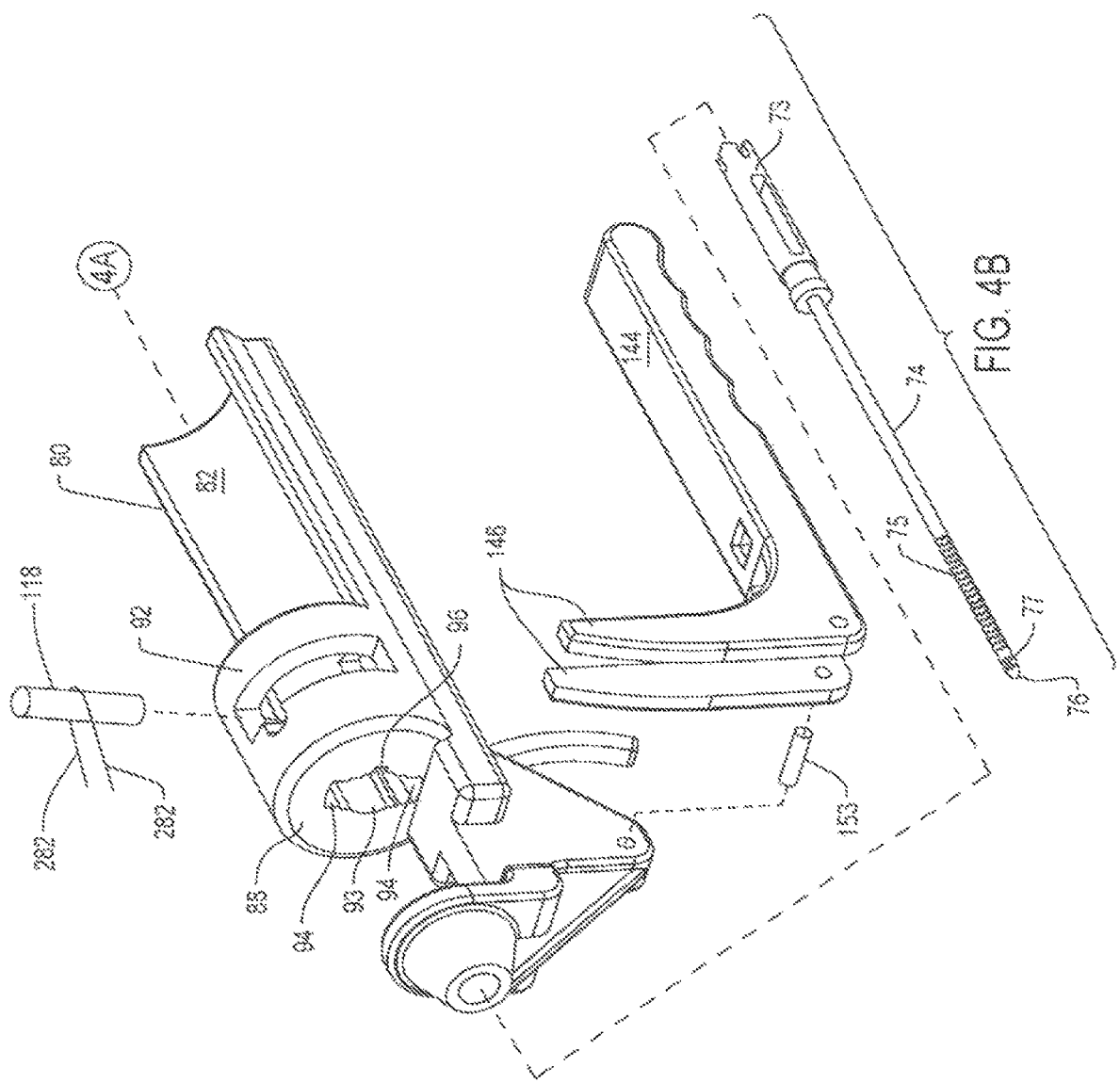

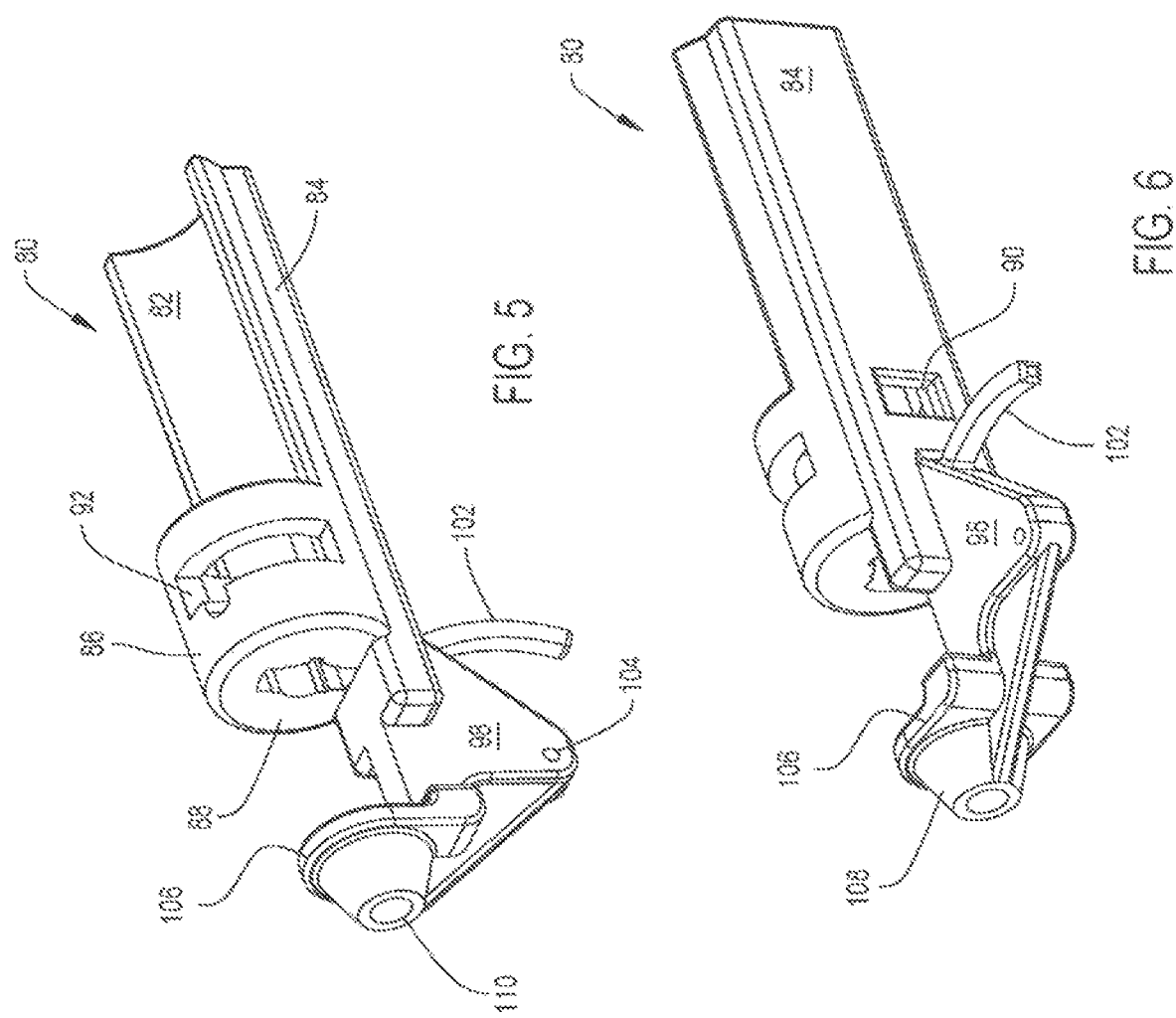

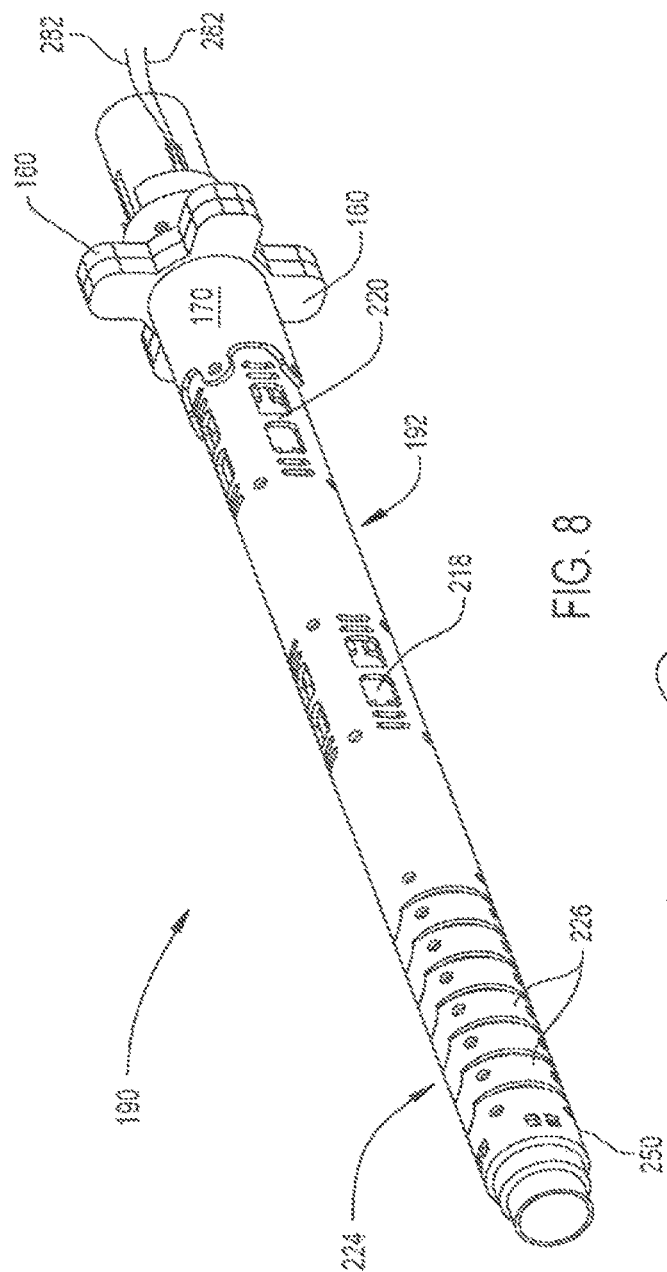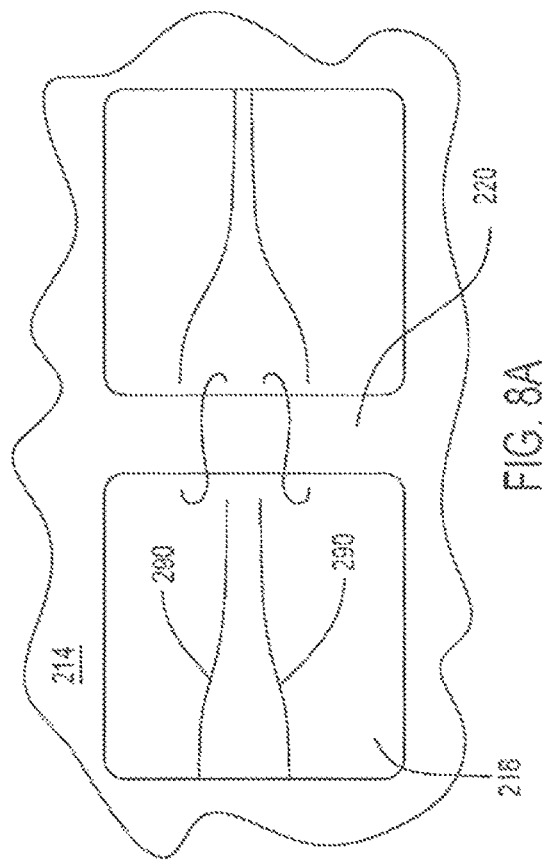
FIG. 8
FIG. 8A

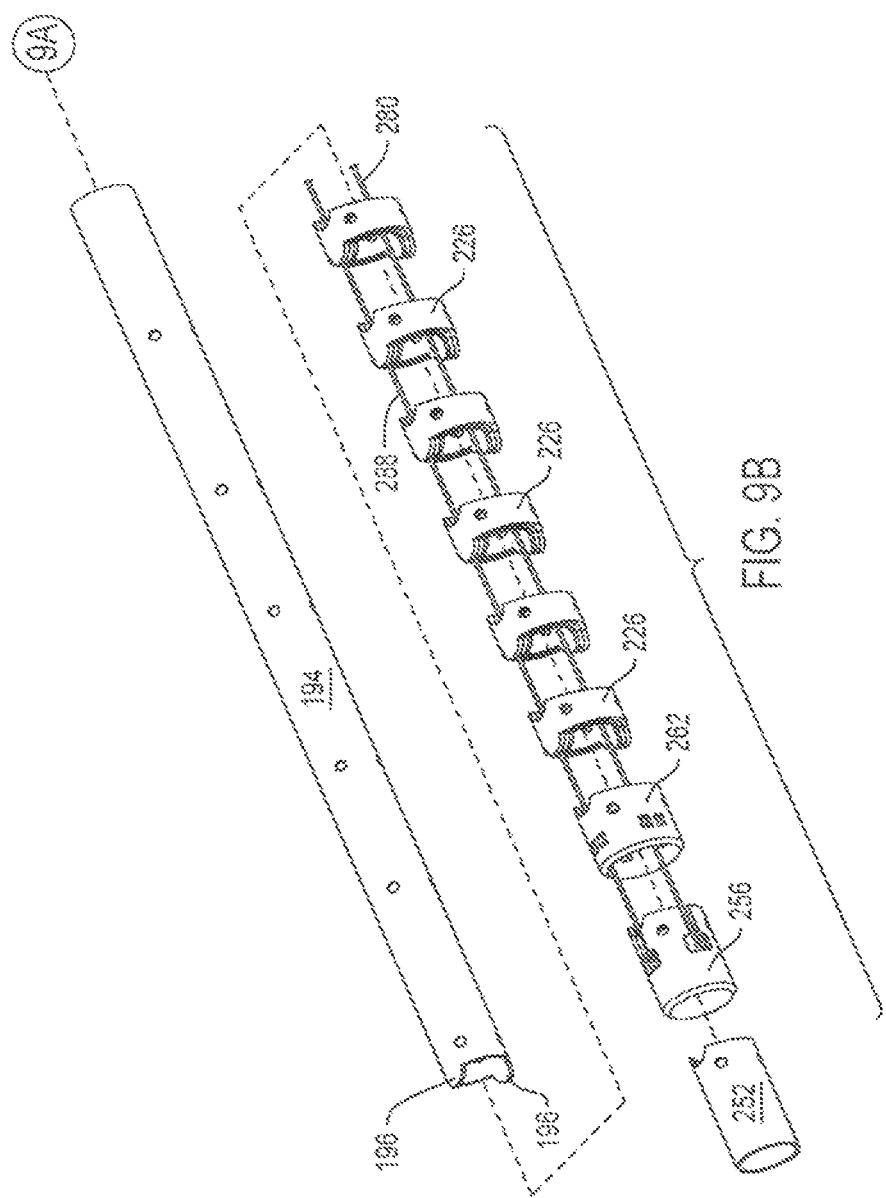

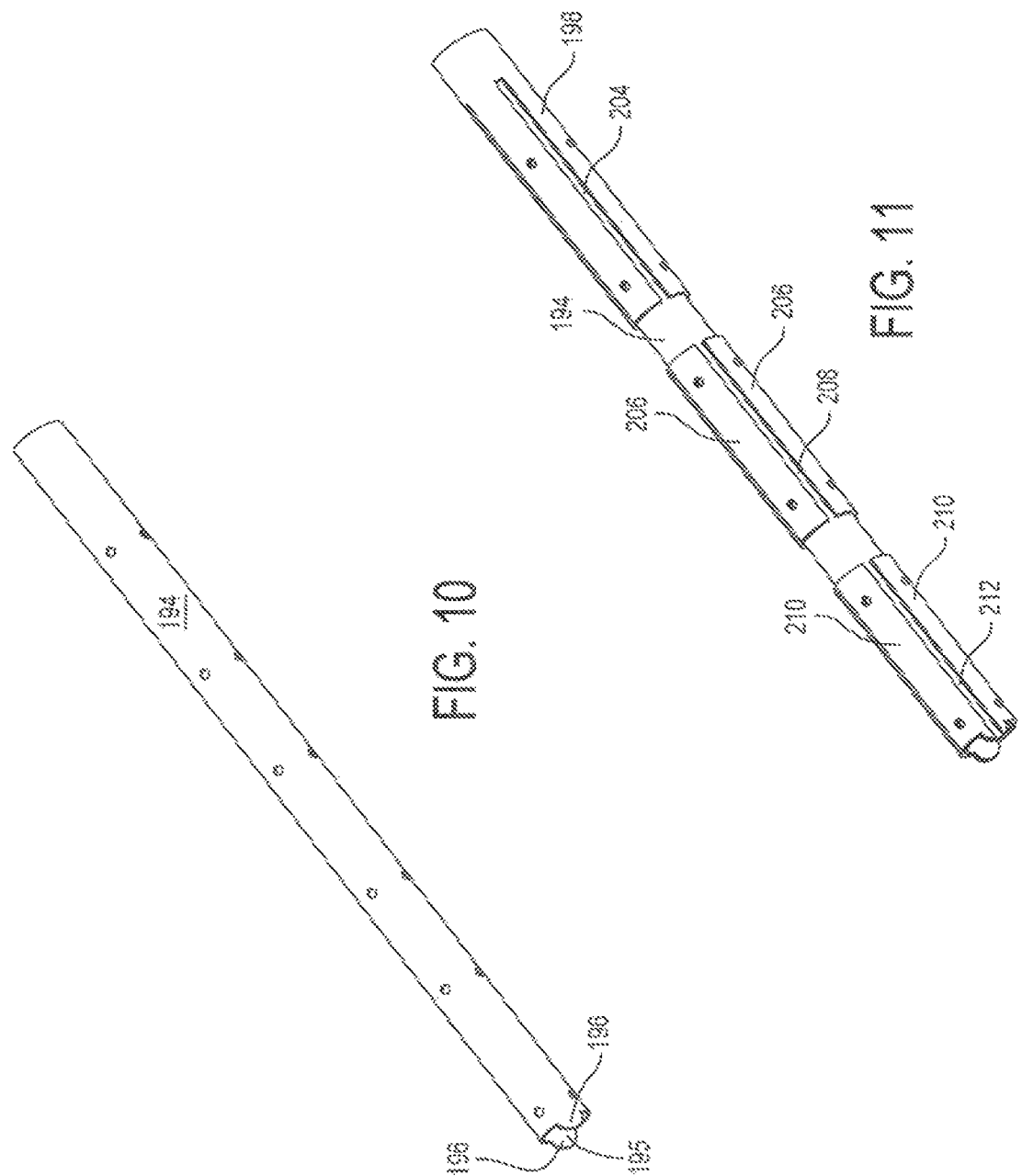

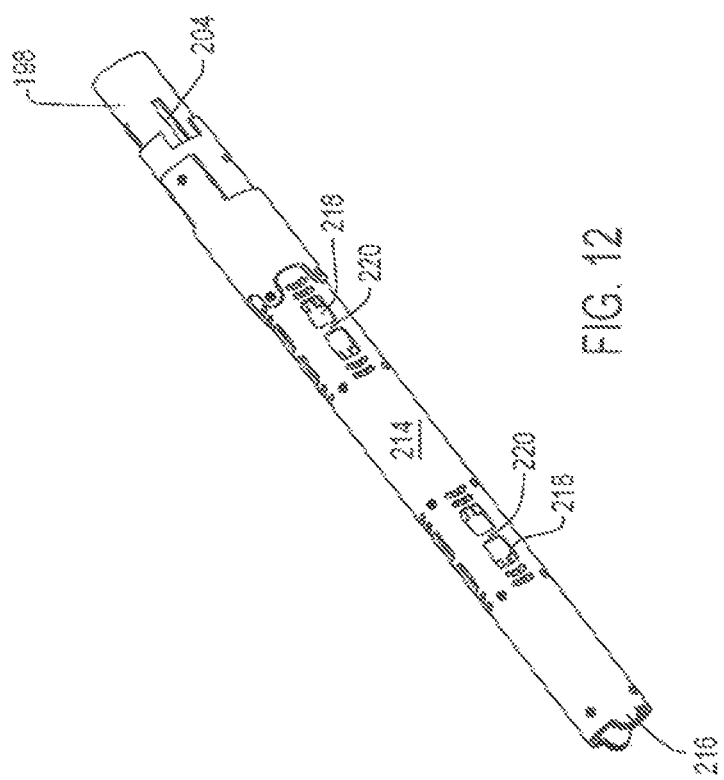

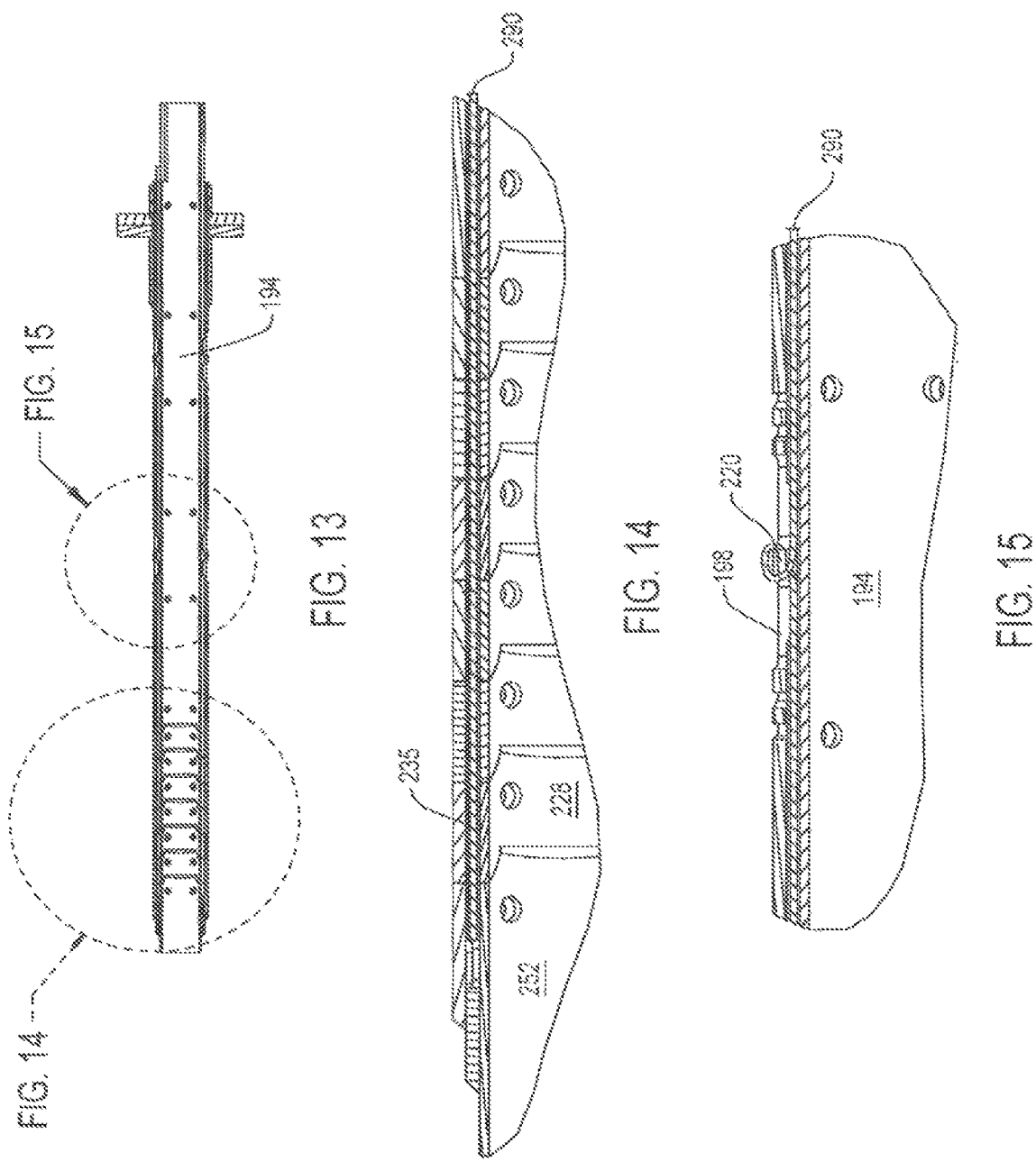

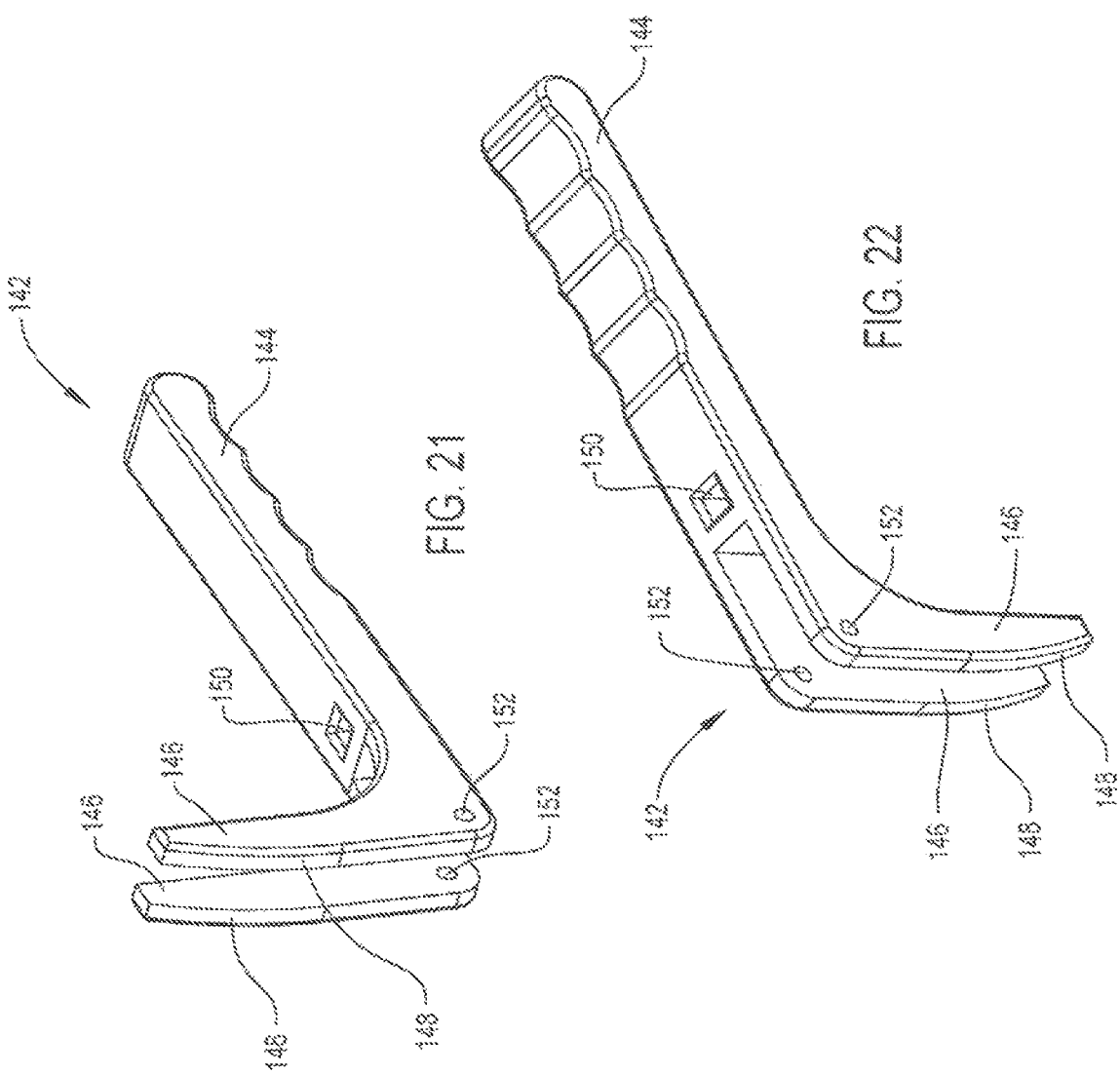

SURGICAL TOOL INCLUDING AN INELASTIC AND ELASTIC CABLE TO BE TENSIONED TO IMPART A BEND

CROSS REFERENCE TO RELATED APPLICATIONS

This application is a continuation of copending U.S. patent application Ser. No. 16/587,823, now U.S. Pat. No. 11,457,902, filed Sep. 30, 2019, which is a continuation of U.S. patent application Ser. No. 15/489,132 filed Apr. 17, 2017, now U.S. Pat. No. 10,492,771, which is a divisional of PCT Application No. PCT/US2015/055624, filed Oct. 15, 2015, which claims priority to and all the benefits of U.S. Provisional Patent Application No. 62/065,628, filed Oct. 18, 2014, the entire contents of each being hereby incorporated by reference.

FIELD OF THE INVENTION

This invention is generally related to a medical or surgical tool that has an elongated shaft that can be bent to have a specific curvature. More particularly, this invention is directed to a tool with an elongated shaft that can be bent and that, when exposed to a load, resists buckling.

BACKGROUND OF THE INVENTION

A number of different medical and surgical tools include elongated shafts. A device for performing a medical or surgical procedure or a diagnostic evaluation is located at the distal end of the shaft, the end furthest from the practitioner using the tool. Providing the tool with shaft makes it possible to position the device that performs the procedure in the patient at a location that is 5 cm or more below the skin. The presence of the shaft makes it possible to perform a procedure on the patient without having to make a large incision so that the location at which the procedure is performed is essentially exposed to the ambient environment. Exemplary surgical tools with this type of shaft include burs, shavers, forceps, staplers, ultrasonic vibrators, RF tissue ablation and/or cauterization electrodes and cameras used to view inside the patient.

When this type of tool is used, the tool is often directed to the site at which the procedure is to be performed through a portal or channel in the patient. This portal may be one that is established as part of the procedure. Alternatively, the portal may be part of a channel that naturally exists in the patient. Nostrils are an example of one set of naturally present portals in a patient It is a known practice to provide this type of tool with a shaft that, once inserted in the patient is selectively curved. This is because there are many situations in which it is simply not desirable or even possible to perform the procedure by simply positioning the distal end of the shaft at the site at which the procedure is performed. For example, sometimes the shaft is inserted into a portal that curves. This means that after at least partially inserting the shaft in the portal, the practitioner needs to bend the tool shaft so as to further insert the shaft. During a procedure, the practitioner may want to curve the distal end of the shaft to obtain a minimally obstructed view of the application of the working component to the site to which the component is applied.

One species of a tool with a selectively curved shaft is provided with multiple adjacent segments that are bendable relative to each other. At least one cable extends through the shaft to at least the most distally located segment. Some tools are provided with two, three or four cables. The cables are connected to an anchor adjacent the proximal end of the shaft, the end opposite the distal end. The anchor rotates around at least one axis. A number of these tools are further designed so that the position of the anchor is manually set. The practitioner bends the tool by rotating the anchor to cause the selective tensioning and flexing of the cables. This flexing and tensioning of the cables places a longitudinal load on the shaft from the distal end of the shaft. This load is not uniformly imposed on the shaft. There is an arcuate section of the shaft that is subjected to greater loading. The portions of the segments forming this part of the shaft so loaded are compressed or bent towards each other. The bending of these segments is what provides the shaft with its practitioner selected curve.

The above-described tools are able to bend in real time. These tools are sometimes useful for applying a head to tissue so that head is laterally spaced from an extension of the longitudinal axis that extends from the housing or body of the tool.

Nevertheless, there are some tools for which to date, it has been difficult to incorporate a shaft that is bendable in real time. One class of tools that it has proven difficult to use with this type of shaft are tools that include heads that are subjected to significant side loading or radial forces. One species of this class of tool are powered surgical tools. These powered surgical tools includes shaver heads and bur heads. When the head of this type of tool is pressed against tissue, the tissue imposes an appreciable amount of force against the advancement of the head. This force is on a line that, relative to the longitudinal axis of the head, extends radially inwardly towards the center of the head. The force thus appears as the side loading of the head. When the head extends from a rigid shaft, the rigid shaft is able to withstand the opposition this force places on the advancement of the head.

However, when the head is located on the end of known bendable shafts, the slack cables do not hold the longitudinally adjacent arcuate sections of the shaft through which these cables extend against each other. The application of a force against the shaft head causes these individual sections of the shaft to shift position relative to each other. The collective movement of these sections of the shaft causes the shaft to deform from the bend desired by the practitioner.

Further, some tools when activated, apply an added force to the head of the tool shaft. These tools are tools that, to function, are rotated. Examples of such tools include burs and shavers. The rotation of these tools places a tangential force on the tool head. For the reasons set forth above, the bendable shafts of known tools often deform from their desired bends in response to the application of these tangential forces.

Eventually, the flexure of the shaft away from the desired shape may be so great that the shaft no longer has the shape required in order to apply the tool head to the tissue. When this event occurs, the practitioner is required to interrupt the application of the tool and reset the tool so the shaft has the desired curvature. Only after the shaft bend is reset is the practitioner able to resume the procedure. Having to so interrupt the performance of the procedure to repetitively reset the shaft curvature goes against one of the goals of modern surgical practice; a procedure should be performed as quickly as possible. This is a desirable goal because it both minimizes the likelihood the exposed tissue is open to infection and the amount of time the patient is held under anesthesia.

Further, after the tool shaft is bent to perform the procedure it is typically desirable to unbend the tool back to a shape that is straight or nearly straight. This unbending is required in order to remove the tool from the portal through which the tool was inserted in the patient. For many current tools, to unbend the tool it is necessary for the practitioner to do more than just release the tension of the cable subjected to tension. It is also necessary for the practitioner to place a tension on the cables previously allowed to go slack. This is because the tensioning of these cables is what causes the previously bent portions of the shaft to return to a shape that is at or near straight. Requiring the practitioner to apply use his/her fingers to apply the force needed to so straighten the tool further contributes to physical fatiguing of the hand.

SUMMARY OF THE INVENTION

This invention relates to a new and useful surgical tool with a shaft that can be selectively bent and then straightened. The tool of this invention is designed so that after the tool shaft is bent, tension is imposed on the tool head around substantially the whole of the circumference of the head. This tension allows the head to resist side or radial loading that, if not opposed, can cause the flexure of the shaft away from the shape desired by the practitioner.

The tool of this invention includes a shell or a body. An elongated shaft extends from the shell. The shaft is bendable. That is, the shaft can flex away from the longitudinal axis that extends forward from the shell. The shaft, in addition to being bendable, is mounted to the shell to move proximally and distally, longitudinally, relative to the shell. Plural cables extend forward from the proximal end of the shaft. The cables are arcuately spaced from each other around the shaft. Each cable has a proximal end that is at fixed location adjacent the proximal end of the shaft. Each cable has a distal end connected to the distal end of the shaft. At least one cable is what as referred to as an inelastic cable. The inelastic cable is formed from material that while able to bend, when subjected to tension does not appreciably stretch. At least one cable is what as referred to as the elastic cable. The elastic cable is formed from material that in addition to being flexible, stretches when subjected to tension and, upon release of the tension, returns to its original length.

The tool of this invention further includes a steering assembly. The steering assembly is typically mounted to the shell. The steering assembly is assembly that, when actuated, causes the shaft to move forward of the shell.

A working head is located at the end of distal end of the shaft. This head may be device that is applied to tissue to perform a medical procedure. Heads include: rotating shavers; rotating burs and drill bits. Other heads include forceps. Still other heads include electrosurgical tips that emit RF energy or thermal energy. Still other heads emit photonic (light) energy. Other working heads are designed to form diagnostic procedures as opposed to therapeutic procedures.

The tool of this invention is designed so that when the shaft is straight, all the cables are in tension. The cables thus hold shaft in the unbent shape. Typically, when the tool is not bent the tool is straight. To bend the tool, the steering assembly is actuated to cause the forward movement of the shaft. When the shaft moves forward, the elastic cable stretches. The inelastic cable does not, however, undergo the same expansion. Instead, the inelastic cable inhibits the extension of the portion of the distal end of the shaft to which the inelastic cable is attached. As a consequence of this portion of the shaft being inhibited from advancing, portions of the shaft bendable section rotate around each other. The rotation of these sections of the shaft around each other cause the shaft to develop the practitioner desired bend.

The bending of the tool shaft does, however, not cause the cables to go slack. Instead, each of the cables remains in tension around the distal end head of the tool shaft. The shaft head is thus, around the whole of the head, urged proximally towards the shell or body of the tool. When the shaft head is subjected to side loading, external radial force, the forces urging the head towards the tool shell resist this laterally directed force. The resistance of the shaft head to this force prevents this force from flexing the shaft away from the bent shape desired by the practitioner.

Once the tool is used, it is typically necessary to return the shaft to the unbent shape. This is accomplished by the releasing of force applied to the steering assembly. The release of this force allows the potential energy stored in the cables as result of the increased tensioning of the cables to be released. The release of the potential energy in the cable causes the elastic cable to return to the original length. The collective release of force by all cables causes the longitudinal translation of tool shaft back to the unbent position.

In some versions of this invention, the shaft consists of a main tube and plural links. The main tube is attached to the shell. The links are located forward of the main tube. The head is located forward of the links.

In some versions of the invention, the tool includes a single inelastic cable and plural elastic cables.

In some versions of the invention, the shaft includes an inner tube or ring. An outer tube or ring is disposed over the inner tube or ring. The cables are disposed between the tubes or the rings.

In some versions of the invention the tool shell and tube are designed to removably receive another type of tool. The second tool has its own shaft that, while flexible, is not steerable. Attached to the end of the shaft of the second tool is the component that functions as the shaft head. The second tool is coupled to the tool of this invention. As part of this tool coupling process the flexible shaft of the second tool is seated in the selectively bendable tool of this invention. The selectively bendable shaft, the shaft to which the cables are attached, can be considered the outer shaft of this assembly. The flexible but not steerable shaft of the second tool can be considered an inner shaft of the assembly. The head attached to this inner shaft is the head of the tool. In order to position the head, the steering assembly is actuated. The actuation of the steering assembly bends the outer shaft. The bending of the outer shaft bends the inner shaft so as position the head against the tissue on which the procedure is to be performed.

BRIEF DESCRIPTION OF THE DRAWINGS

The invention is pointed out with particularity in the claims. The above and further features and advantages of the tool of this invention are understood from the following Detailed Description taken in conjunction with the accompanying drawings in which:

FIG. 3 is a cross sectional view of the tool of this invention;

FIG. 4 is an assembly view depicting how FIGS. 4A and 4B are arranged to form an exploded view of the tool of this invention;

FIG. 5 is a perspective view of the tool shell when view from the front;

FIG. 6 is a perspective view of the tool shell when viewed from rear;

FIG. 7 is a cross sectional view of the tool shell and the lever of the steering assembly;

FIG. 8 is a perspective view of the tool shaft;

FIG. 8A is an enlarged view of the tool shaft depicting how the elastic cables are anchored to the shaft FIG. 9 is an assembly view depicting how FIGS. 9A and 9B are assembled to form an exploded view of the tool shaft;

FIG. 10 is a perspective view of the inner tube of the tool shaft;

FIG. 11 is a perspective view of the inner tube of FIG. 10 showing the bushings disposed over the tube;

FIG. 12 is a perspective view of the tool shaft;

FIG. 13 is a cross sectional view of the tool shaft;

FIG. 14 is a first enlarged portion of the cross sectional view of FIG. 13;

FIG. 15 is a second enlarged portion of the cross sectional view of FIG. 13;

FIG. 21 is a first perspective of the steering lever;

FIG. 22 is a second perspective view of the steering lever;

DETAILED DESCRIPTION

I. Construction

Figure 1:
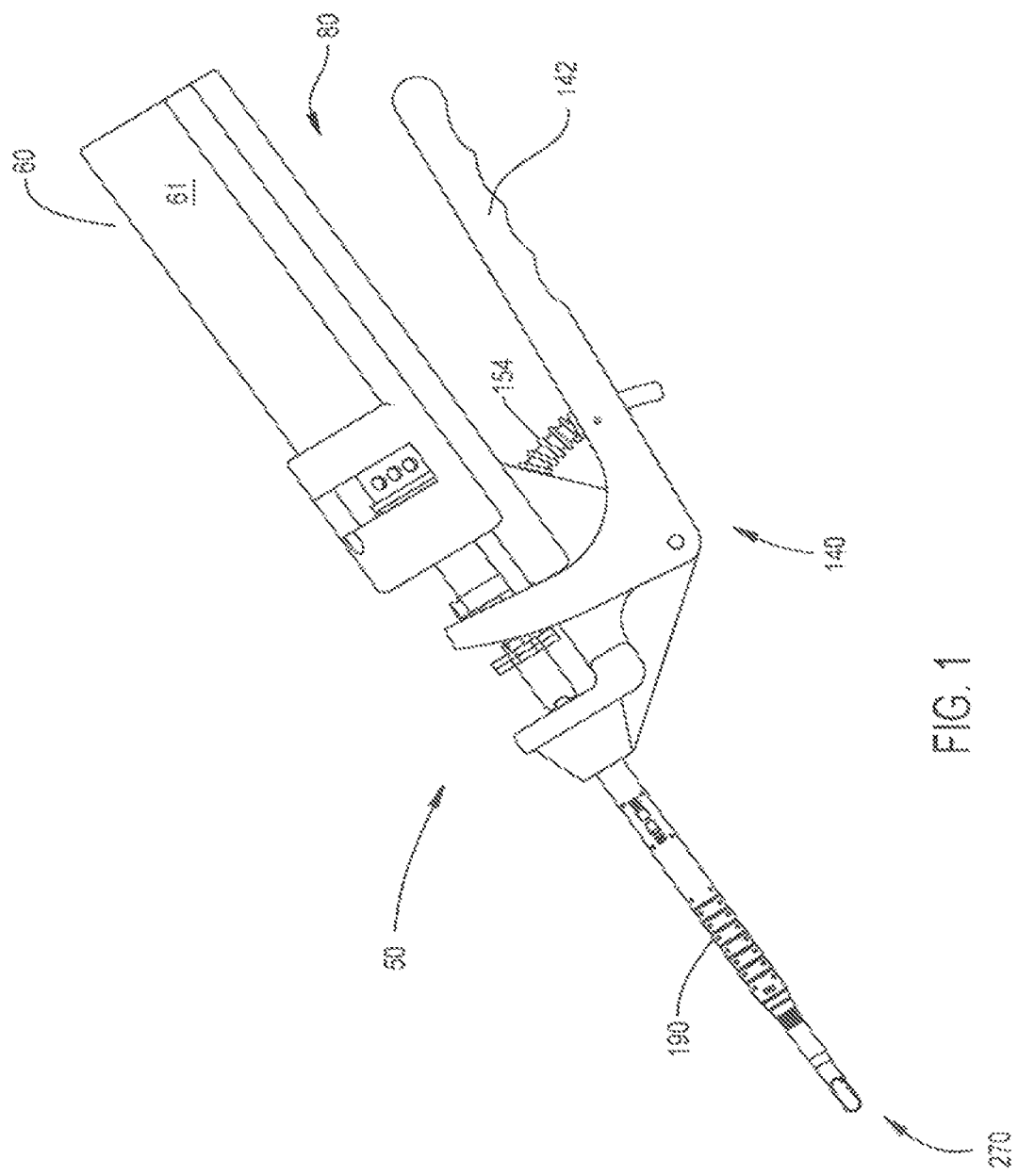
FIG. 1 is a side view of a tool of this invention including the attached removable power generating unit.
Figure 2:
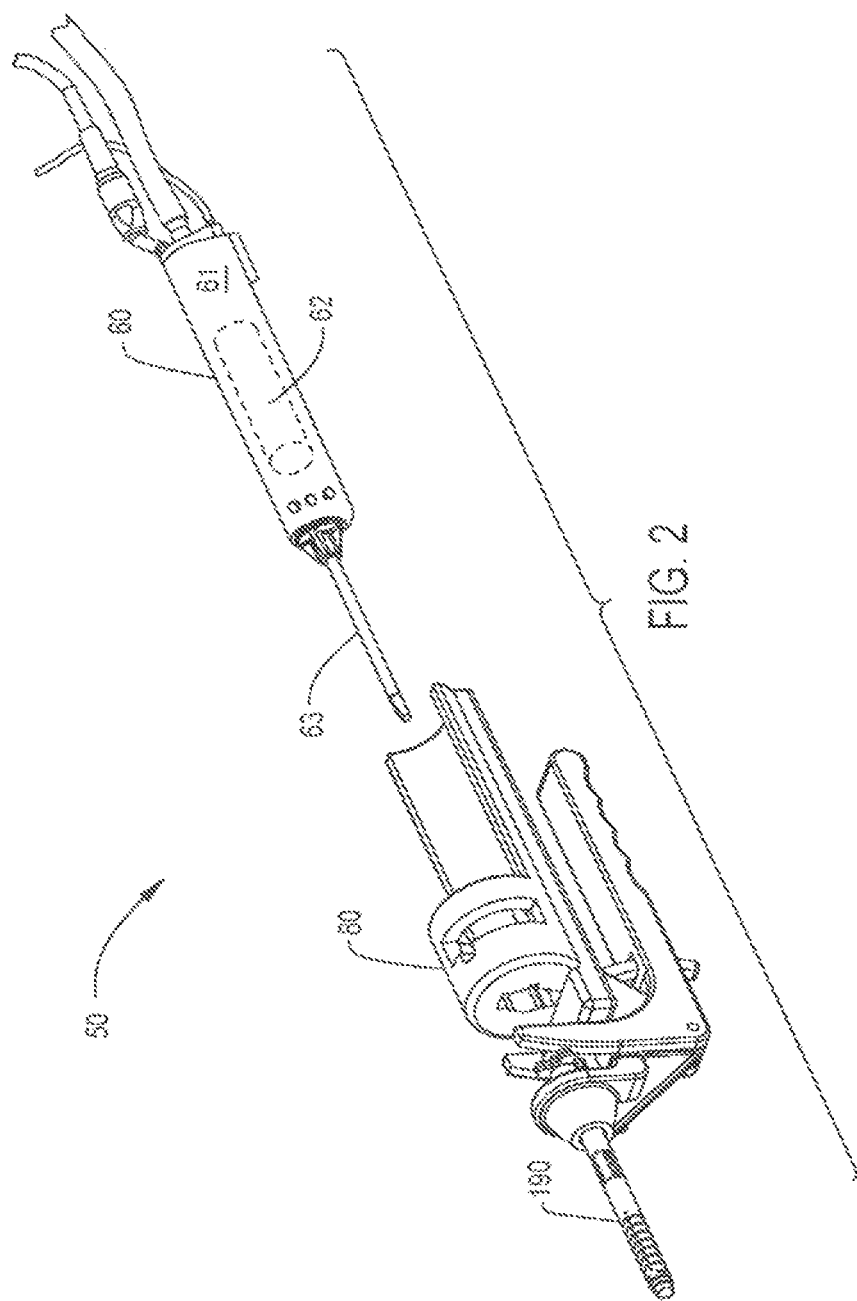
FIG. 2 is a partially exploded view of the tool of this invention including the removable driver.

FIGS. 1 and 2 depict a surgical tool 50 of this invention. Tool 50 includes a working head 270 designed to be applied to a site on a patient in order to perform either a therapeutic or diagnostic procedure. Working head 270 is located forward of the distal end of a tool shaft 190. (Here "distal" is understood to mean away from the practitioner holding the tool 50; toward the site to which the head is applied. "Proximal" is understood to mean close to the practitioner holding the tool 50; away from the site to which the head is applied.) Tool shaft 190 is flexible or bendable. The proximal end of the tool shaft 190 is fitted to a shell 80. Shell 80 is the body or housing of the tool 50. A steering assembly 140 is also mounted to the shell 80. Steering assembly 140 is actuated by the practitioner using the tool 50 to control the bend in the tool shaft 190.

A driver/receiver 60 is shown mounted to the shell 80. The driver/receiver 60 is connected to the working head 270 through the tool shaft 190. When the working head 270 is a device applied to tissue to perform a procedure, the driver/receiver 60 is the component of tool 50 that actuates the head. When the working head 270 is a device that is applied to tissue for diagnostic purposes the driver/receiver 60 may be employed to: actuate the head; process signals received by the head; and/or display information obtained by the head. In the illustrated version of the invention, driver/receiver 60 is removably mounted to the shell 80.

Figure 4A:
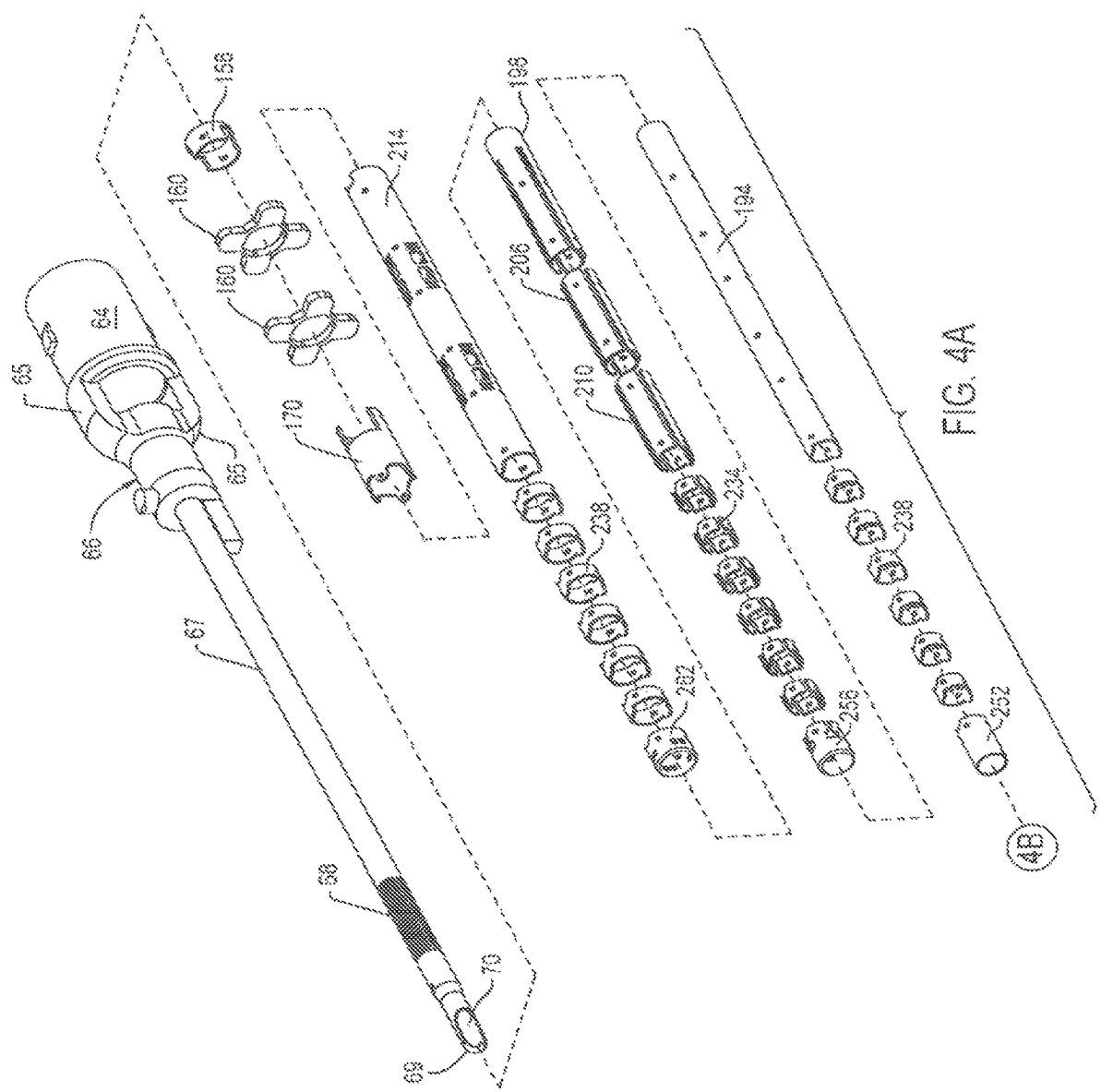

In the illustrated version of the invention, driver/receiver 60 is a powered surgical tool known as a shaver. Shaver 60 includes a handpiece 61. Internal to the handpiece 61 is a motor 62 represented by a phantom cylinder. A shaving tube assembly 63 extends distally forward from the handpiece 61. Shaving tube assembly 63 is dimensioned to seat in and extend forward of the tool shaft 190. The shaving tube assembly 63, as seen in FIGS. 4A and 4b, includes an outer tube 67 and an inner tube 74. Tubes 67 and 74 both have sections that are flexible. The outer tube 67 is part of an assembly that includes a tubular shaped outer hub 64. Outer hub 64 is formed with features configured to cooperate with components internal to the handpiece 61 to releasably hold the outer hub static to the handpiece. Two posts 65 extend distally forward from the outer hub 64. Posts 65 are diametrically opposed to each other relative to the common proximal-to-distal longitudinal axis through the outer hub 64 and outer tube 67. At their distal ends, posts 65 taper inwardly towards each other. A tubular shaped core 66 extends forward from the distal ends of posts 65. The outer tube 67 extends forward from core 66. Tube flexible section 68 is located towards the distal end of the tube 67. The outer tube 67 is formed with a head 69 located forward of flexible section 68. While the tube head 69 is closed at the distal end, the tube head is formed with a window 70 that is located along the side of the head.

The inner tube 74 is part of an assembly that includes an inner hub 73. The inner hub 73 is formed with features that facilitate the coupling of the inner hub to the motor 62 so the inner hub rotates upon actuation of the motor. Inner tube 74 has a flexible section 75 located slightly proximal to the distal end of the tube. The inner tube 74 is formed with a distally located head 76. Tube head 76 is formed with a window 77 that is located proximal to the distal end of the head. The inner tube 74 is dimensioned to seat in and rotate in the outer tube 67.

While not illustrated it should be understood that the portions of the tube heads 69 and 76 that define windows 70 and 77, respectively, are formed with sharp edges that collectively form a scissor assembly. This scissor assembly formed by the tube heads 69 and 76 is the working head 270 of the tool 50.

The exact structure of the shaver 60 and the shaving tube assembly 63 are not part of the present invention. An exemplary shaver 60 and shaving tube assembly 63 are disclosed in U.S. Pat. No. 6,985,071, the contents of which are explicitly incorporated herein by reference.

When tool 50 of this invention is assembled, handpiece 61 is removably attached to the shell 80. The shaving tube assembly 63 is disposed in the tool shaft 190. Tube heads 70 and 76 extend forward of the tool shaft 190.

From FIGS. 5, 6 and 7 it can be seen that shell 80 is a single piece unit. The shell 80 is formed to have a cradle 82. In cross section, in planes perpendicular to the proximal to distal longitudinal axis along the shell, the cradle 82 appears arcuate in cross section. The concave surface of the cradle 82 is shaped to receive the curved body of the shaver handpiece 61. Shell 80 is further formed to have a rib 84 that extends longitudinally along the outer concave surface of the cradle 82. Rib 84 has a planar outer surface (not identified). Rib 84 protrudes a short distance forward of the shell cradle 82. A curved collar 86 extends over the cradle 82. The collar 86 is disposed over the distal end of the cradle 82. Collectively, the cradle 82 and collar 86 are dimensioned to receive the front portion of shaver handpiece 61. A plate 88 is disposed over the proximal end of collar 86.

Shell 80 is further formed to have two windows 90 and 92. Window 90 extends through rib 84 and the portion of the cradle 82 immediately above the rib. Window 90 opens into the space enclosed by cradle 82 and collar 86. Window 92 is formed in collar 86. Window 92 opens into the same general space internal to the shell 80 into which window 90 opens. Windows 90 and 92 are present to accommodate and allow access to components associated with shaver 60. These include components used to control the actuation of the shaver 60.

The shell plate 88 is formed with an opening, best seen in FIG. 4B, that extends proximally to distally through the plate. The opening has a center section 93 that is generally circular in shape. Two diametrically opposed notches 94 extend radially outwardly from the opening center section 93. One notch 94 extends downwardly from opening center section, towards the shell rib 84. The opposed notch 94 extends outwardly from the opening center section 93 away from the rib 94. Notches 94 are dimensioned to receive posts 65 integral with the shaver assembly outer tube 67. A third notch, notch 96, also extends radially outwardly from the opening center opening 93. Shell 80 is formed so that notch 96 is centered around a radial line that is perpendicular to the common axis around which the notches 94 are centered.

A beam 98, also part of shell 80, extends distally forward from rib 84. Beam 98 is planar in structure and is disposed in a plane perpendicular to the plane of the outer surface of the rib 84. The beam 98 is triangular in shape so as to have a vertex that is located forward of and below the distal end of the rib 84. The leading section, the distal section of the beam 98 is of reduced side-to-side thickness than the more proximal portions of the beam. The shell 80 is formed so that a post 102 extends downwardly from the beam 98. The post 102 extends downwardly from the proximally facing surface of the beam. This is the surface of the beam that, extending distally from where the beam extends from rib 84, extends downwardly. Post 102 is curved. More particularly, as the post 102 extends downwardly from beam 98, the post curves distally forward. The shell 80 is further formed so that a bore 104 extends side to side through the beam 98. Bore 104 is located immediately above the bottommost vertex of the beam 98.

The shell 80 includes a bracket 106. Bracket 106 extends upwardly from the distal end of the beam 98. Generally, the bracket 106 is planar and lies in a plane that is perpendicular to both the plane of rib 84 and the plane of beam 98. The shell 80 is formed so that the bracket 106 is spaced forward from the shell collar 86.

A head 108 projects distally forward from the shell bracket 106. The shell 80 is shaped so that the head 108 is generally in the form of a truncated conic shape. Specifically, extending distally from bracket 106, the diameter of head 108 decreases. Shell 80 is further shaped so that a bore 110 extends proximally-to-distally through bracket 106 and head 108. Bore 110 is dimensioned so that the tool shaft 190 can both seat in and slidably move in the bore.

A pin 118, seen in FIG. 4B, is mounted to the shell 80. The pin 118 is seated in a notch that forms part of the window 92 in the shell collar (notch not identified). Tool 50 is constructed so that pin 118 is located behind the notch 96 formed in shell plate 88.

The tool shaft 190, as seen in FIG. 8, includes a proximally located rigid section 192. A bendable section 224, also part of the tool shaft 192, is attached to and located forward of the rigid section 192. A shaft head 250, which is rigid, is located forward of the bendable section 224. Head 250 forms the distal end of the tool shaft 190. From FIGS. 4A, 9B and 10, it can be seen that the tool shaft rigid section 192 includes a cylindrically shaped inner tube 194. The inner tube 194 is formed from stainless steel. A bore 195, identified in FIG. 10, extends axially through the tube 194. Inner tube 194 is formed so that two tabs 196 extend forward from the distal end of the main body of the tube, (tube main body not identified). Each tab 196 is semicircular in shape. The inner tube 194 is formed so that tabs 196 are diametrically opposed to each other relative to the proximal-to-distal longitudinal axis through the tube 194.

Seen in the Figures are small holes that extend radially through the main body of the inner tube 194. Similar holes are seen in the below-described bushings 198, 206 and 210 and the outer tube 214. These holes are present for manufacturing purposes only and are otherwise not material to the present invention.

Plural bushings 198, 206 and 210, are disposed over the outer surface of the inner tube 194 as seen in FIG. 11. Each of the bushings 198, 206 and 210, is formed from stainless steel. A proximal bushing 198 extends forward from the proximal end of the inner tube 194. Bushing 198 is formed to have four equiangularly spaced apart slots 204, one slot 204 seen in FIG. 11. Spaced forward of the proximal bushing are four arcuately shaped middle bushings 206 (two bushings 206 seen in FIG. 11). The middle bushings 206 are spaced apart from each other around the inner tube 194. The bushings 206 are spaced apart from each other so as to define between each adjacent pair of bushings a slot 208, (one slot 208 identified). Each slot 208 is collinear with a slot 204 integral with the proximal bushing 198.

Four arcuately shaped distal bushings 210 are also disposed around the inner tube 194 (two bushings 210 seen). Distal bushings 210 are spaced distally away from the middle bushings 206 so there is gap between the distal ends of the middle bushings 206 and the proximal ends of the distal bushings 210. Each distal bushing 210 extends to the distal end of the inner tube 194. A portion of each distal bushing 210 also extends over one of the tabs 196 that extends forward from the inner tube 194. The bushings 210 forming each pair of adjacent distal bushings 210 are arcuately spaced apart from each other to define a slot 212 between the bushings. Each slot 212 is collinear with a slot 204 and a slot 208.

The shaft outer tube 214, seen in FIG. 12, tightly fits over the shaft inner tube 194 and bushings 198, 206 and 210. Outer tube 214 is formed from the same material from which the inner tube 194 and bushings 198, 206, 210 is formed. The components forming the tool shaft 190 are formed so that, when the shaft is assembled, the proximal end of the outer tube 214 is located distally forward of the proximal end of the inner tube 194. More particularly, the proximal end of the outer tube is located forward of the proximal portion of the slots 204 defined by the proximal bushing 198. Outer tube 214 is further formed to define to two notches 215 that extend forward from the proximal end of the tube 214 (one notch 215 seen in FIG. 9A). Notches 215 are diametrically opposed to each other relative to the longitudinal axis through the tool shaft 190. Outer tube 214 extends to the distal ends of the inner tube 194 and the distal bushings 210. The outer tube 214 is formed with semicircular tabs 216, (one tab 216 seen in FIG. 12). Outer tube tabs 216 extend over the inner tube tabs 196.

The outer tube 214 is formed to have plural rectangularly shaped windows 218. In the depicted version of the invention, in each 90° arcuate section of the outer tube there are two windows 218. Within each arcuate section of the outer tube 214 the two windows 218 are longitudinally spaced apart from each other. Within each arcuate section the major axes of the two windows 218 are longitudinally aligned. The outer tube is further formed so that a web 220 extends arcuately across each window. Each web 220 divides the window 218 into a proximal portion and a distal portion. Individual window portions not identified.

Also not identified and not material to the present invention are small slots formed in the outer tube. These slots are located proximal and distal to each window 218.

When tool shaft rigid section 192 is assembled, the components are arranged so that the proximal webs 220 integral with the outer tube 214 are located above the space forward of the distal end of bushing 198 and proximal to the distal ends of bushings 206. The distal webs 220 integral with the outer tube 214 are located above the space distal to the distal ends of bushings 206 and proximal to the proximal end of bushings 210.

Figure 16:
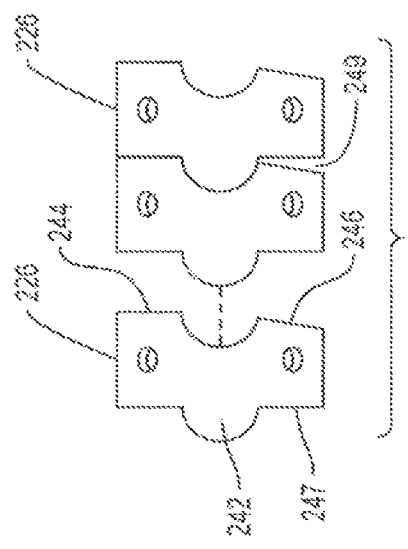
FIG. 16 is a perspective view of a single intermediate link of the tool shaft.
Figure 17:
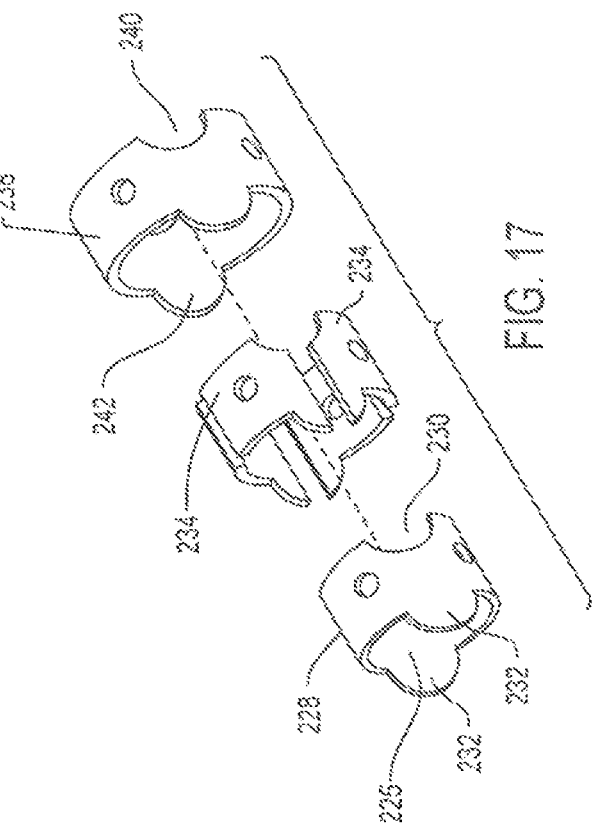
FIG. 17 is a an exploded view of the components forming the intermediate link.
Figure 18:
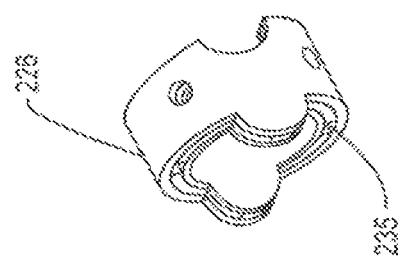
FIG. 18 is a side plane view of plural intermediate links, one link being spaced from the adjacent links.

Plural series connected links 226 form the shaft bendable section 224. Each link 226, as seen in FIGS. 16-18, includes an inner ring 228. Each inner ring 228 has the same inner and outer diameters as the shaft inner tube 194. The inner ring 228 is shaped to define two socket spaces 230 that extend distally forward from the proximal end of the ring. The inner ring 228 is further shaped to have two tabs 232 that extend forward from the distal end of the ring. Tabs 232 are identical to tube tabs 196. Sockets 230 are dimensioned to receive tabs 196 or 232. Each ring tab 232 is longitudinally aligned with a separate one of the sockets 230.

The inner ring 228, the spacers 234 and the outer ring 238 the form each link 226 are shown as having radially extending through holes (holes not identified). The holes are present for manufacturing purposes and otherwise not material to the present invention.

Four arcuately shaped spacers 234 are disposed over the outer surface of the inner ring 228. Spacers 234 are arcuately spaced apart from each other around the inner ring so as to define a channel 235 (one channel identified in FIG. 16) between each adjacent pair of spacers. Channels 235 extend proximally to distally along the length of the link 226. It will be noted that one channel 235 extends above each of the inner ring tabs 232.

An outer ring 238 is tightly disposed over the inner ring 228 and the spacers 234. Outer ring 238 has the same inner and outer diameter as the shaft outer tube 214. The outer ring 238 is formed to define the socket spaces 240 similar to the inner ring sockets 230. Outer ring 238 has tabs 242 that overlie the inner ring tabs 232.

As seen best in FIG. 18, the components forming each link 226 are further formed so that the proximally directed end of the link does not completely lie in a plane perpendicular to the longitudinal axis through the link. Instead, the proximal portion of each link 226 has two faces 244 and 246. In FIG. 18 the edges of faces 244 and 246 are called out. Each face 244 extends between adjacent ends of the sockets 230 and 240. One face, face 244, lies in a plane that is perpendicular to the proximal-to-distal longitudinal axis through the link 226. The opposed face, face 246, lies in a plane that is offset from the plane of face 244. More specifically, face 246 lies in a plane that, extending radially away from the longitudinal axis of the link 226, extends distally forward. At the distal end of the link there is a single face, face 247. Face 247 lies in a plane perpendicular to the longitudinal axis through the link 226. Face 247 is interrupted by the distal projection of link tabs 232 and 242.

Figure 19:
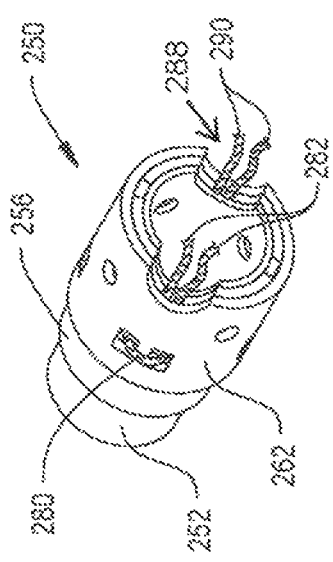
FIG. 19 is a perspective view of the distal end head of the tool shaft.
Figure 20:
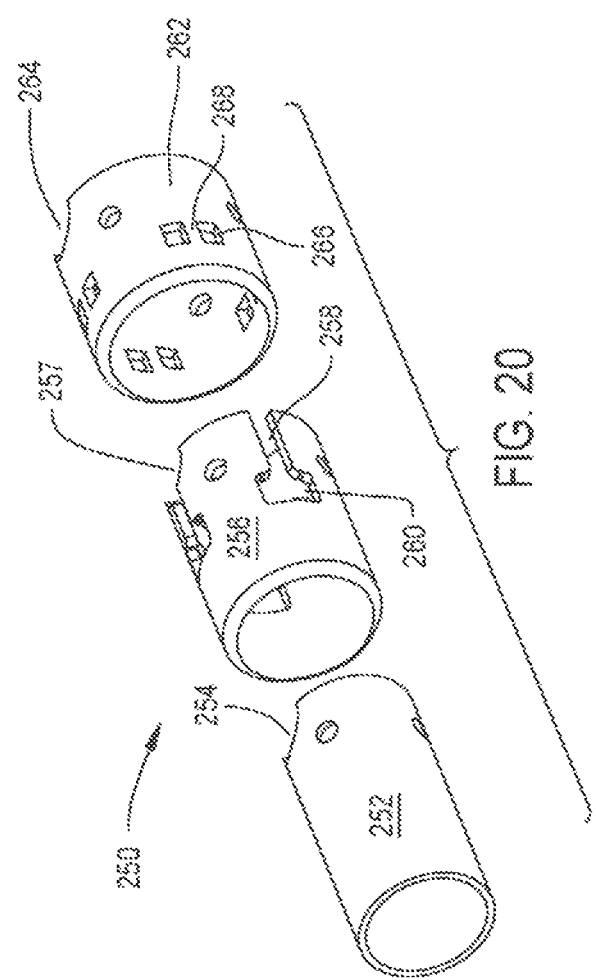
FIG. 20 is an exploded view of the tool shaft head.

The shaft head 250, as seen in FIGS. 19 and 20, includes an inner tube 252. Inner tube 252 has the identical inner and outer diameters of inner tube 194. Inner tube 252 is formed with two semi-circular sockets 254, (one socket 254 seen in FIG. 19). Sockets 254 are dimensioned to receive the tabs 232 of the distalmost link 226.

The inner tube 252 as well as the below described bushing 256 and outer tube 262 that form the shaft head are formed with radially extending through holes (not identified). These through holes are present for manufacturing purposes and are otherwise not relevant to the invention.

Generally, cylindrical bushing 256 is disposed over the outer surface of the inner tube 252. In the depicted version of the invention, the distal end of bushing 256 is located proximal to the distal end of the head inner tube 252. Bushing 256 is formed with a four equiangularly spaced apart slots, (one slot is clearly illustrated in FIG. 20). Each slot has a proximal section, slot section 258, that extends from the proximal end of the bushing 256. The slot proximal section 258 is relatively narrow in arcuate width. The slot proximal section opens up into a slot distal section 260. The slot distal section 260 has a relatively large arcuate width. Bushing 256 is further formed to have two sockets 257, (one socket identified). Sockets 257 correspond in shape to sockets 254 integral with the inner tube 252. Two of the slots formed in the bushing 256 are arranged so that the slot proximal sections 258 actual extend distally forward from the sockets 257.

The head outer tube 262 is disposed over the inner tube 252 and surrounding bushing 256. In the depicted version of the invention, the distal end of the outer tube 262 is spaced proximal to the distal end of the bushing 256. Outer tube 262 is formed with sockets 264 that correspond to link outer ring sockets 240. The outer tube is further formed to have four equiangularly spaced apart windows 266, (one window 266 identified in FIG. 20. The major axes of windows 266 are centered on a plane that is perpendicular to the proximal-to-distal longitudinal axis through the shaft head 250. The components forming the shaft head 250 are further formed so that when the head is assembled, each window 266 is disposed over the distal section 260 of one of the slots forming in the bushing 256. The outer tube 262 is further formed so a web 268 bisects each window 266. Each web 268 is centered on the proximal-to-distal minor axis that extends through the associated window 266. Each inner tube socket 254 is in registration with a corresponding bushing socket 257 and outer tube socket 264.

When the tool shaft 190 is assembled it should be understood that each tab seats in appropriate socket. Each linear set of slots 204, 208 and 210 is aligned with a set of link channels 235. Each link channel 235 opens into a separate one of the narrow width slot sections 258 internal to the shaft head 250. The contiguous void spaces of the adjacent inner rings 228 define a bore 225 that extends through the bendable section, (a section of the bore 225 identified in FIG. 17).

In the described version, an inelastic cable 280, seen in FIGS. 4B, 8 and 9B, extends through the tool shaft 190. Inelastic cable 280, as implied by its name, is formed from material that when subjected to an axial load, does not appreciably stretch. Material from which inelastic cable 280 may be formed from is a nickel titanium alloy (Nitinol) or stainless steel. The inelastic cable 280 is formed from two strands 282. As seen in FIG. 19, the distal end of the inelastic cable 280 is wrapped around the outer surface of the web 268 that crosses one of the windows 266 in the shaft head outer tube 262. The opposed strands 282 of the cable extend first through slot section 260 and then into slot section 258 of the shaft head 250. From the shaft head 250, the cable strands extend through the set of aligned channels 235 internal to the links 250. From links 250, strands 282 extend through the set of slots 212, 208 and 204 aligned with link channels 235. From FIG. 8 it is seen that strands 282 exit proximally rearward from the slot 204 in which the strands are seated. From the tool shaft 190, cable strands 282 extend through the notch 96 formed in the plate 88 integral with the shell. The cable strands 282 are tied to pin 118.

More specifically, it should be understood that the inelastic cable 280 extends through the slots 204, 208, 212 and link channels 235 that, in FIG. 18, would appear at the bottom of the link 226. Thus, when the tool is assembled links are arranged so that the proximally directed link faces 246 are the link faces closest to notch 96. When the links are arranged in series and each tab seats in the appropriate socket, there is small longitudinal spacing 249, seen in FIG. 18, between the distally directed face 247 of one link and the adjacent proximally directed face 246 of the distally adjacent link. Each spacing 249 is what allows each link to rotate around the adjacent link.

In the described version of the invention, three elastic cables 288 extend from the shaft head 250 to shaft rigid section 192. For ease of illustration, only a single elastic cable is shown in FIGS. 9B and 19. Elastic cables 288 are formed from material, that, when subjected to axial loading, stretch and store potential energy. Upon the release of the axial load, the potential energy stored in the cable 288 is released. Each elastic cable 288 is formed from two parallel strands 290 as seen FIG. 8A.

The distal ends of cables 288 are wrapped around the three remaining webs 268. The remaining webs 268 are the webs 268 around which the inelastic cable 280 is not wrapped. Cable strands 290 pass through the adjacent bushing slots and link channels 235 in a manner similar to that in which the inelastic cable strands pass through the same voids. The cable strands then enter the associated slots 212 internal to the shaft rigid section 192.

From the slot 212 the two strands 290 extend under the distalmost outer tube window 218 in registration with the slot. As depicted in FIGS. 8A and 15, the strands are then looped distally over the web 220. The strands then extend through the adjacent slot 208. From the slot 208 the strands are wrapped around the web 220 associated with the associated proximally located window 218. The proximal ends of the strands may terminate in the slots 204. The wrapping of the cable strands 290 around the webs 220 holds the proximal portion of each elastic cable 282 static to the shaft rigid section 192.

It should further be understood that tool 50 is constructed so that elastic cables 282 are each slightly in tension.

The tool steering assembly 140 includes a lever 142 that is mounted to shell 80. The lever 142, now described by reference to FIGS. 4B, 21 and 22 is a generally L-shaped structure. The lever 142 includes an elongated beam 144 that is normally angled to be offset from a line that is parallel to the longitudinal axis through the shell. Two arms 146 extend first distally forward from and then perpendicularly upward from beam 144. The lever 142 is formed so that the arms 146 are parallel and spaced apart from each other a sufficient distance so the arms can be located on the opposed sides of the shell beam 98. Each arm 146 has a distally directed face 148. The arms are further formed so that at the free ends of the arms, the faces 148 taper rearwardly, proximally away from the most forward portions of the faces.

Lever 142 is further formed to have a through opening 150 in the beam 144. Through opening 150 is dimensioned to receive the post 102 integral with the tool shell 102. Each arm 146 is formed with an opening 152. The openings 152 are located adjacent the corner between the downwardly directed face of the arm and the adjacent distally directed face 148. Openings 152 are coaxial.

When tool 50 is assembled, the lever 142 is pivotally attached to the shell 80. More particularly a pivot pin 153, seen in FIGS. 3 and 4B, extends through beam bore 104 as well as lever openings 152 pivotally holds the lever 142 to the shell 80. When the tool is so assembled, post 102 extends through lever opening 150. A spring 154 seen only in FIG. 1, is disposed between over the post 102. Spring 154 is in compression between shell beam 98 and lever beam 144. The spring 154 thus places a force on the lever that normally holds the lever beam 144 at an acute angle that is approximately 5 to 20° offset from the longitudinal axis through the shell 80. The force spring 154 places on the lever can be overcome with manual force.

Figure 9A:
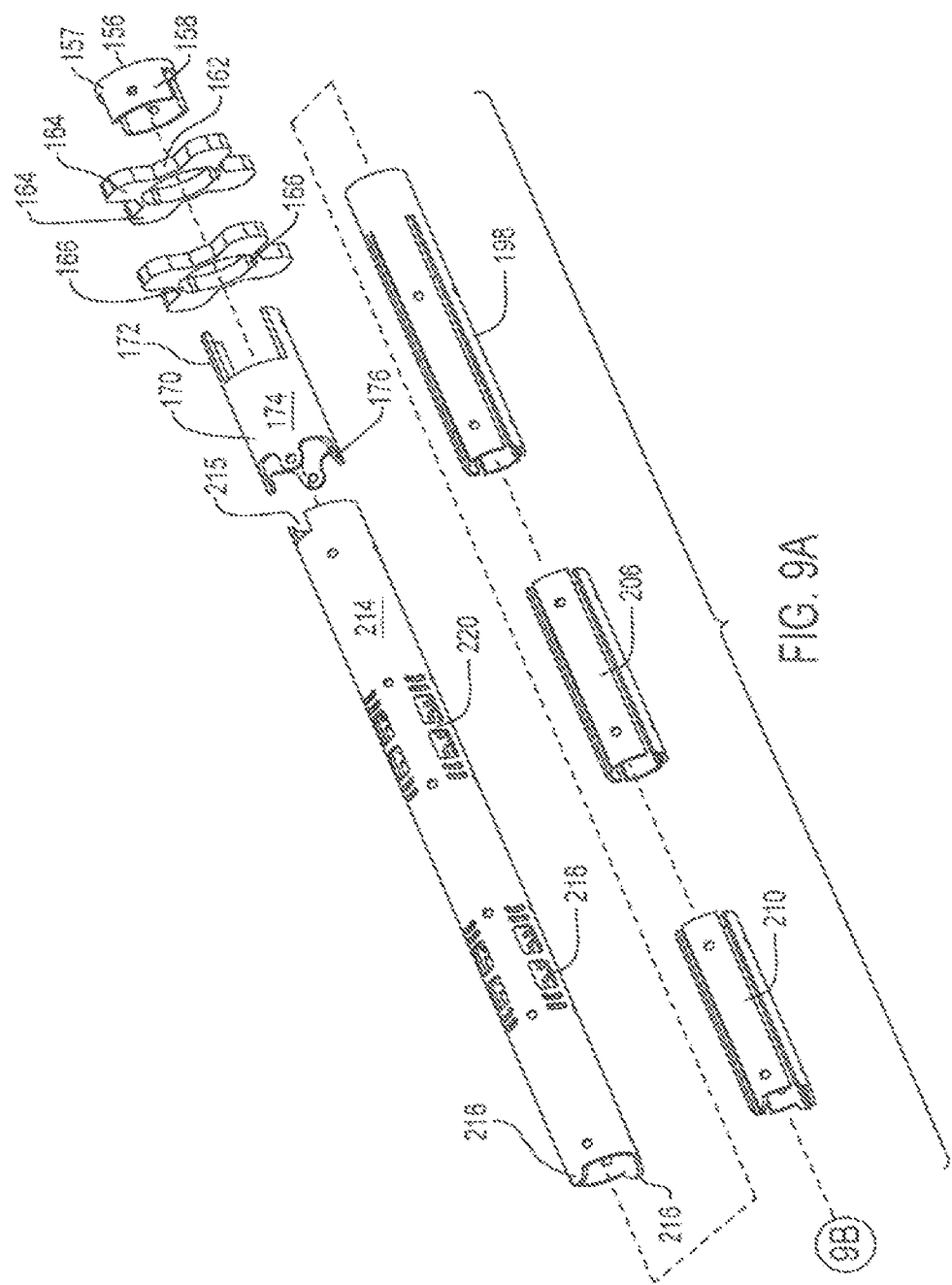

Two collars 156 and 170 and at least one actuator ring 160 and a collar 170, seen best in FIGS. 8 and 9A, are also part of steering assembly 140. In the Figures, two actuator rings 160 are shown. Each actuator ring 160 includes a ring shaped hub 162. The hub 162 has a center opening (not identified) designed to facilitate fitting of the hub over shaft outer tube 214. Four equiangularly spaced apart tabs 164 extend radially outwardly from ring hub 162. The actuator ring is further formed so that the hub 162 has two diametrically opposed notches 166. Notches 166 are contiguous with and extend radially outwardly from the hub center opening.

Collars 156 and 170 hold the actuator ring 160 static to the tool shaft 190. Collar 156 has a tube like base 157. Two arcuately shaped diametrically opposed arms 158 extend forward from the base 157.

Collar 170 is located forward of the actuator ring 160. The actuator collar 170 has a tubular main body 174. The main body 174 has an inner diameter that facilitates the tight fitting of the collar over the shaft outer tube 214. Diametrically opposed and arcuately spaced apart legs 172 extend proximally from the main body. Collar legs 172 are dimensioned to fit in the notches 166 internal to the actuator ring 160.

Collar 170 is welded or otherwise permanently secured over the proximal end of the shaft outer tube 214. In the illustrated version of the invention, to facilitate this attachment, four tabs 176, one tab identified, project forward from the collar main body 170. Tabs 176 are the portions of the collar welded to tube 214. Each tab 176 is provided with a through hole to facilitate this welding, holes not identified.

Once collar 170 is in place, at least one actuating ring 160 is disposed over the collar legs 172. The actuating ring 160 is positioned to be forward of the distally directed faces 148 of the lever 142. Plural actuating rings 160 may be arranged in series as seem in FIGS. 8 and 9A. This is to ensure that when the lever is in the static position, beam 144 is approximately 20° to the shell longitudinal axis, the proximally directed surface of the tabs 166 of an actuating ring abut or are essentially spaced less than 2 mm forward of the lever distally directed faces 148.

Once the at least one actuating ring 160 is in place, collar 156 is positioned adjacent the proximal end of the proximal most ring. Collar 156 is welded to the outer tube 214. The distal ends of the collar arms 158 abut the adjacent proximally directed surface of the adjacent collar hub 162. Not identified are the openings in the collar base 157 that facilitate the welding of the collar 156 to the outer tube 214.

When tool 50 is assembled, the portion of tool shaft 190 to which collars 156 and 170 and actuator rings 160 are mounted are located distal to shell collar 86 and proximal to bracket 106. The actuator rings 160 are located immediately forward of arms 146 integral with lever 142.

II. Operation

Tool 50 is readied for use by fitting the shaver 60 and shaving tube assembly 63 to, respectively, the shell 80 and tool shaft 190. As part of this process, shaver tube 67 is inserted through shell collar 86 into the tool shaft 190. The rigid sections of tubes 67 and 74 seat in the bore 195 internal to the shaft rigid section 192. Tube flexible sections 68 and 75 seat in bore 225 of tube flexible section 224. As part of this process, outer hub 64 can only be positioned so that the associated posts 65 seat in the notches 94 formed in shell plate 88. Owing to how the components are formed, means heads 69 and 76 of the shaving tube assembly can only have one of two rotational orientations relative to tool shaft 190. The shaving tube heads 69 and 76 can be oriented so as to be directed towards notch 96 integral with the shell 80. When the shaving tube heads 69 and 76 are so oriented, the heads are in the closest position to the inelastic cable 280. The second rotational orientation of the shaving tube heads 69 and 76 is 180° from the first rotational orientation. The shaving tube heads face away from shell notch 96 and are spaced as far as possible from the inelastic cable 280.

Regardless of the orientation of the shaving tube assembly 63, the components are arranged so that shaving tube assembly heads 69 and 76 project distally forward and out of the open end of tool shaft head 250. It should further be understood that when then shaving tube assembly 63 is disposed in the tool shaft 190, the flexible sections 68 and 75 of the individual shaving tubes 67 and 74, respectively, are disposed within bendable section 224 of tool shaft 190.

In the rest state, inelastic cable 280 and elastic cables 288 are each slightly in tension. The cables 280 and 288 collectively impose a slight force around the whole of the circumference of the shaft head 250. This force urges head 250 proximally rearward. The forces the cables 288 place on the shaft head 250 are imposed about a substantial portion of the circumference of the head. Shaft head 250 therefore places a small force on the links 226. The links 226 are thus compressed between the shaft rigid section 192 and the shaft head 250. Links 226, which forms the shaft bendable section 224 are therefore normally linearly aligned, straight.

Tool 50 is then directed to the site to which the tool head 270 is to be applied. Often the tool shaft 190 is inserted through a portal towards the tissue on which the procedure is to be performed or on which the head 270 will perform a diagnostic function. This portal may be a natural portal in the body of the patient. Alternatively, an access tube may be inserted into the patient to define the portal. An access tube typically has a diameter wider than that of the tool shaft to facilitate positioning of the shaft.

Owing to curves in the portal to the tissue to which the head 270 is to be applied it may be necessary to bend the tool shaft 190. The practitioner accomplishes this task by squeezing the steering lever 142. Specifically, the lever beam 144 is depressed to bring the beam into an orientation more parallel to the longitudinal axis through the shell 80. In FIG. 3, this would appear as counterclockwise rotation of the lever 103 around pin 153.

Figure 23:
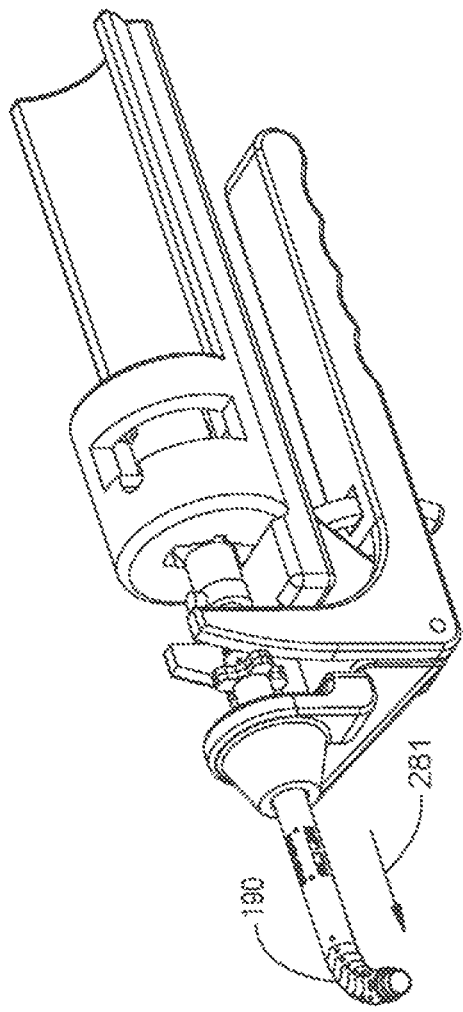
FIG. 23 is a perspective view of when the tool shaft of the tool of this invention is bent.
Figure 24:
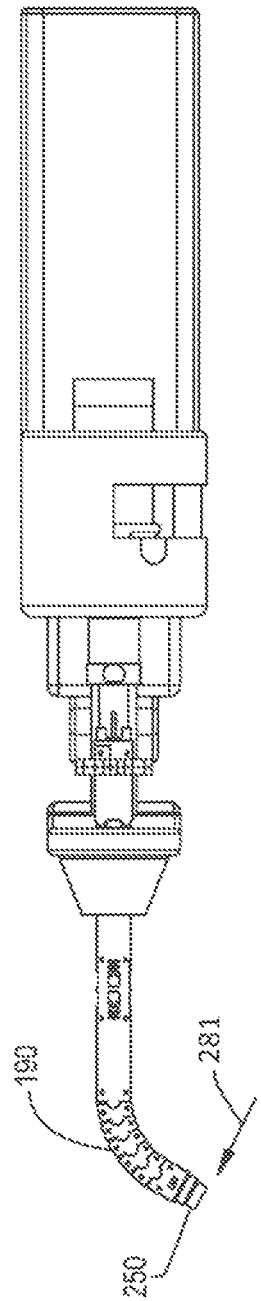
FIG. 24 is a top plan view of when the shaft of the of this invention is bent.

The resultant counterclockwise, generally distally directed movement of the lever arms 146 causes the distally directed faces 148 of the arms to abut and push the actuator rings 160 forward. The forward movement of the actuator rings causes a like forward movement of the tool shaft 190. The unyielding nature of inelastic cable 280 inhibits the advancement of the arcuate section of the shaft head 250 to which the cable 280 is attached. Shaft head 250, in response to the forward advancement of the rest of the shaft, rotates around the link tabs seated in the sockets integral with the head. The continued extension of the tool shaft 190 results in a cascading effect wherein each link 226 rotates around the proximally adjacent link. As a result of these rotations of the links 226 the shaft flexible section 224 develops a curvature as seen in FIGS. 23 and 24. In FIGS. 23 and 24 the shaver 60 and shaving tube assembly are not present. The radius of curvature is controlled as function of the extent to which lever 142 is pivoted.

While not seen in the drawings it is understood that since the shaving tube assembly 63 flexible sections 68 and 75 are disposed in the shaft flexible sections, these sections of assembly 63 undergo a like flexure. This flexure or bending of the shaving tube assembly 63 results in the positioning of the tool working head 270 adjacent the tissue against which the head is to be applied.

As result of the flexure of the shaft head 250, the linear distances from the sections of the head relative to the shaft rigid section 192 change. More specifically, spaced arcuately away from the inelastic cable 280, the distances around the outer surface of the head relative adjacent outer surfaces of the shaft rigid section increase. This increase is tolerated by the elastic cables 288 because, owing to the material from which they are formed, the cables 288 stretch. The stretching of the elastic cables 288 causes the cables to store potential energy. It should further be understood that as a result of the increase in tension on the inelastic cable 280 there is an increase in the potential energy stored in the inelastic cable 280.

Once the tool shaft 190 is appropriately curved, the practitioner applies the head 270 to the target tissue. Using the driver/receiver, the practitioner performs the desired procedure or performs the desired diagnostic task.

Further in some constructions of the tool of this invention the tool shaft 190 is flexed while the working head 270 is active. For example, if the working head 270 is the above described shaver, the surgeon is able to bend the tool shaft 190 while the shaving tube assembly inner tube 74 is rotating within the outer tube 67. During this bending, the surgeon presses the heads 69 and 76 against the tissue. The shaving heads 69 and 76 thus remove the section of the tissue over which the heads are swept.

After the procedure or diagnostic task is performed, it is often necessary to straighten the tool shaft 190. The straightening is necessary in order to extract the shaft 190 in the portal in which the shaft is inserted. The practitioner straightens shaft 190 of the tool of this invention by backing off if not completely taking off the force applied to the lever. The reduction or termination of this manual force allows the release of the potential energy stored in spring 154. The spring 154 thus rotates the lever 142 clockwise back to the static state for the lever. As a consequence of this rotation of the lever, the force the lever arms apply against the actuator ring 160 is reduced. The reduction of this force reduces the tension applied to the cables 280 and 288. The potential energy stored in the cables 280 and 288 is released. The energy released from the cables 280 and 288 causes the elastic cables 288 to retract back to the original only slightly tensed lengths. The retraction of the elastic cables 288 causes the cables to flex the tool head 250 back to the position in which the tool head is longitudinally aligned with the shaft rigid section 192. By extension, the links 226 rotate back with the tool head to this initial straight orientation. As consequence of this rotation of the links to the straight orientation, the tool shaft 190 is displaced proximally back to the at rest position of the shaft.

During the course of a procedure, the application of the working head 270 to the tissue may result in an inwardly directed force being applied to the shaft head 250. This force is represented by arrow 281 in FIGS. 23 and 24. This force is often a resistive force applied by the tissue against which the tool working member 270 is pressed. Tool 50 of this invention is designed so that when the tool shaft 190 is flexed, bent, each of the cables 280 and 288 are under tension. The cables 280 and 288 are arcuately spaced from each other around the shaft 190. The cables 280 and 288 are in tension. The tension is applied essentially circumferentially around the shaft head 250. The tension thus urges the shaft head 250 proximally against the adjacent link 226. By extension each link 226 is placed in compression against the proximally adjacent link 226. The most proximal link 226 is placed in compression against the shaft rigid section 192. Thus, when subjected to this force, the shaft resists flexure back to the unbent state.

Further since the tension is applied circumferentially around the shaft head 250, the tension holds the adjacent rotating components of the tool shaft, the links 226 and 250 against each other. This facilitates the holding of the desired bend in the tool shaft 190.

There may be situations in which the force applied against the shaft head 250 is so great that the compressive forces the cables 280, 288 place on the shaft bendable section are not able to resist the flexure of the section back to the unbent state. When this situation arises, the practitioner can further extend the shaft relative to the body. This serves to increase the tension on the cables. This increase in cable tension, increases the compressive force the cable place on the shaft bendable section. This increase in this compressive force results in a like increase in the ability of the shaft bendable section to resist the forces that are urging the shaft back to the unbent state.

Further, some working heads, when activated, rotate. An example of such a working head is the above described rotating head 76 integral with the inner tube of the shaving tube assembly. A tangential force is applied to the head as a result of the head rotating against tissue. This force can be thought of as a force that is directed inwardly toward the head along a line that does not intersect the center of the head. The tension imposed by cables 280 and 288 of the tool of this invention places a force on the tool head 250 that resists the movement of the tool head in response to the application of this tangential force.

Still another feature of tool 50 is that a single base movement, the distal displacement of the tool shaft 190, is all that is required to place each of the cables 280 and 288 in tension.

III. Alternative Tool

Figure 25:
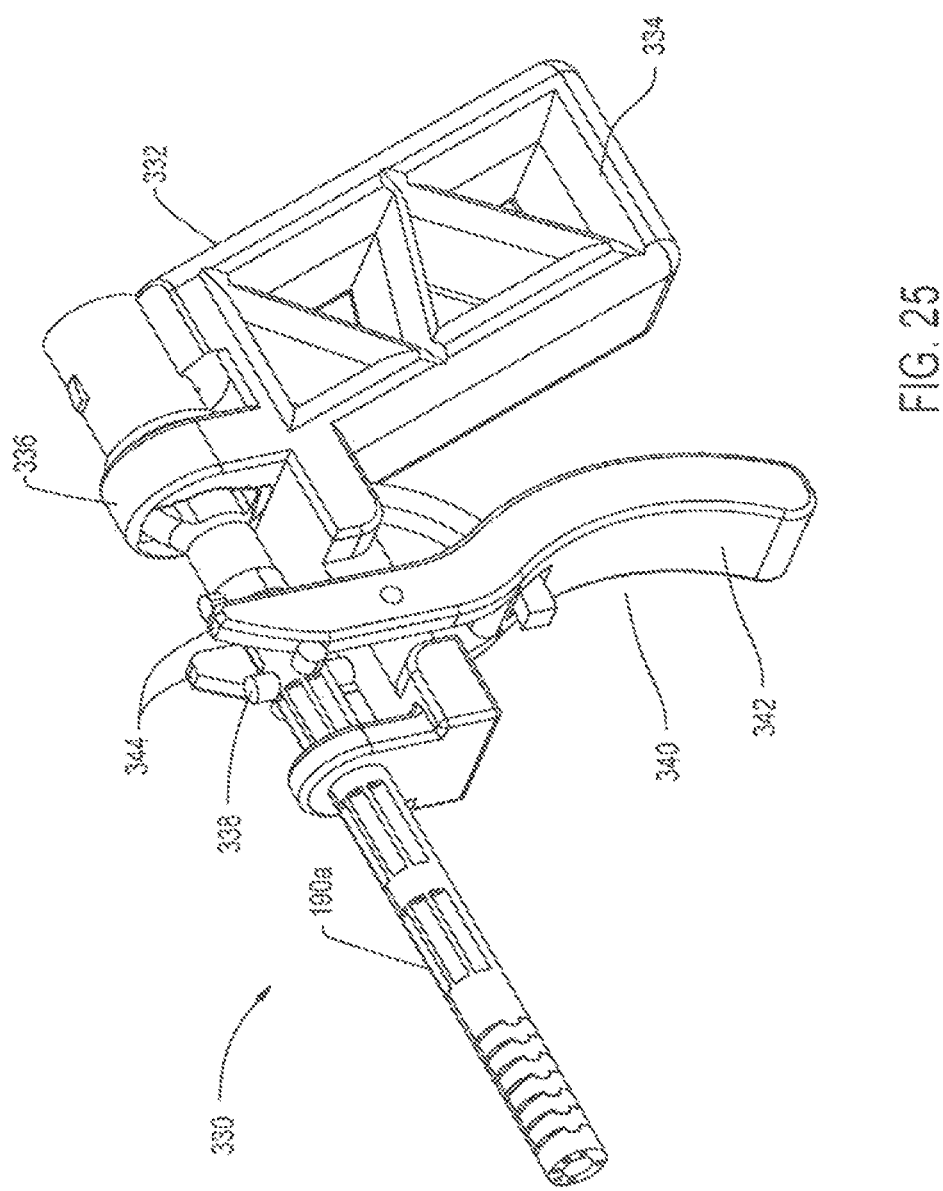
FIG. 25 is a perspective view of an alternative tool of this invention.
Figure 26:
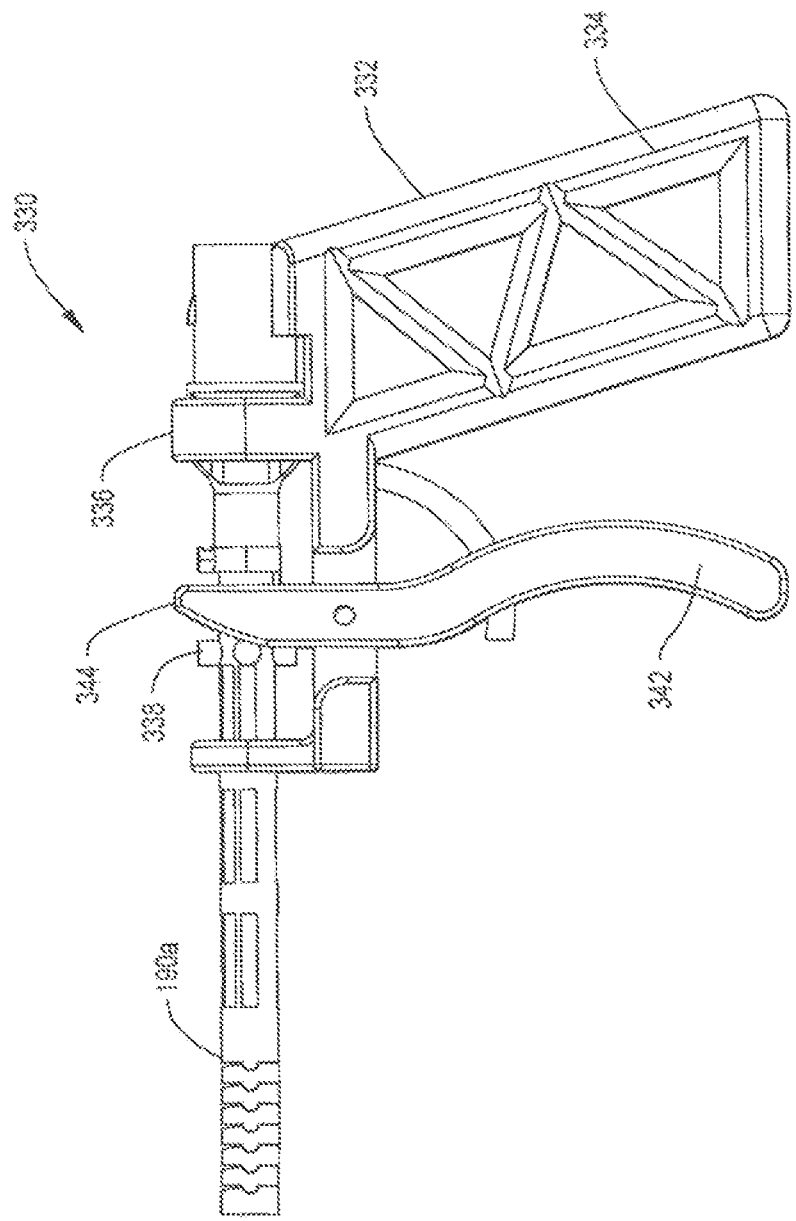
FIG. 26 is a side plan view of the tool of FIG. 26.

As seen in FIGS. 25 and 26 an alternative tool of this invention may have a shape different from what is described above. Tool 330 has a pistol shaped body 332. Tool body 332 is shaped to have a handgrip 334. A barrel 336, also part of the body 332, is located above and extends distally forward of the handgrip.

A tool shaft 190*a*, similar to the previously described tool shaft 190, extends forward from the distal end of the barrel 336. The tool shaft 190*a* is mounted to the barrel for longitudinal movement relative to the barrel. Not illustrated are the cables internal to the barrel analogues to cables 280 and 288 of tool 50. An actuator 338 is mounted to the section of the tool shaft 190*a* located proximal to the distal end of the barrel 336.

Tool 330 includes a steering assembly. The steering assembly of tool 332 includes a lever 340. Lever 340 is pivotally mounted the barrel 336 forward of the handgrip 334. The lever 340 includes a beam 342 that is located below the pivot axis. This beam 340 is located forward of the handgrip 334. Lever 340 includes two arms 344 that are opposed to beam 344. Arms 344 extend on either side of the barrel 336 Beam 344 projects upwardly to the barrel 336. More particularly, the arms are located immediately proximal to and essentially abut actuator 338.

A driver or receiver (not illustrated) is typically mounted to the proximal end of the barrel 336. An elongated member extends through the tool shaft 190*a*. The tool working head is attached to the distal end of this elongated shaft and is located forward of the tool shaft 190*a*.

Tool 330 is used in the same general manner in which tool 50 is used. When there is a need to bend the tool shaft 190*a*, lever beam 340 is pivoted towards the handgrip. Lever arms 344 cause the tool shaft 190*a* to move forward. The cables internal to the tool shaft cause the desired bending of the shaft.

IV. Alternative Versions

The above is directed to specific versions of the invention. Alternative versions of the invention may have features different from what has been described.

For example, the bendable section of the tool shaft may be of different construction. In some versions of the invention, this portion of the tool may have more or less links than described. Alternatively, this version of the invention may be an assembly that does not include plural individual components. For example, in one alternative version of the invention, the bendable section comprises a helical wrap. The wrap is formed with spaces between the individual turns so as to facilitate the bending of the wrap. Alternatively, the bendable section may be formed out of material that owing to its nature is flexible. Stiffeners may be embedded in the flexible material. The inelastic and elastic cables cooperate to compress the stiffeners against each other. As a result of the stiffeners being so compressed, the bendable section of the shaft resists bending from the desired shape when exposed to side loading.

It should therefore be appreciated that the tool shaft need not always be formed out of metal. In alternative constructions of the invention, the tool shaft may be formed out of plastic or ceramic.

In some versions of the invention, the adjacent links of the bendable section include interlocking teeth. As a result of the links being urged together, the teeth engage. The engagement of the teeth further reduced the likelihood that external forces can cause the bendable section to flex away from the desired curvature.

Likewise, it should similarly be appreciated that there is no need for the tool shaft to be formed out of components that themselves are formed out of inner, middle and outer parts. Any one of the shaft rigid section, the bendable section or the head may be formed as single part. If the component is so formed, the component is typically shaped to have one or more channels through which the cables are, upon assembly of the tool threaded. Depending on the material from which the component is formed, these channels are formed by molding or machining.

In some versions of the invention, the elastic cables are tied off to the shell. A benefit of this version of the invention is that the elastic cables apply a force that normally holds the tool shaft in the proximal position relative to the shell. Further, the means by which the elastic cables are secured to either the rigid section of the tool shaft or shell may vary from what has been described. In some versions of the invention the cable strands may be knotted around a fixed member to facilitate this attachment. Alternatively, the proximal ends of the cable strands may be provided with anchors. These anchors seat in voids shaped to prevent the forward movement of the anchors. Likewise, there is no requirement that either the inelastic or the elastic cables of this invention be multi-strand structures. In some versions of the invention, either one or both of the cable types be a single strand cable. Further, the cable here should be understood to be any elongate, typically thin structure that is flexible and depending on the cable type inelastic or elastic. Thus, the cable for this invention may be formed from a flat strip of metal or plastic that has the desired elastic or inelastic characteristic for the specific function of the cable.

It should of course be understood that the components of the tool may have different shapes from what has been described. For example, in some versions of the invention, the lever 142 may be provided with lugs. These lugs extend distally forward from the forwardly directed faces of the arms 146. When the tool is assembled one of the tabs 164 integral with the actuator ring 162 is disposed between these lugs. The lugs prevent the actuator ring 162 and, by extension, the tool shaft 190 from rotating.

Likewise, there is no requirement that in all versions of the invention the steering assembly include a lever that is manually actuated in order to bend the tool shaft. In some versions of the invention, a finger/thumb pad is attached to the tool shaft. The tool shaft is advanced and retracted as to set shaft curvature by the practitioner pressing a digit against this pad and simply moving the pad back and forth. The movement of the pad results in a like movement of the tool shaft.

In some versions of the invention the structural member integral with the tool shaft that is displaced by the steering assembly to translate the tool shaft may be integrally formed with the tool shaft. This eliminates the need to provide a separate actuator ring and the components that hold the actuator ring static to the tool shaft.

In some versions of the invention, a spring or other biasing member extends between the shell and the tool shaft. This biasing member places a force on the tool shaft to urge the tool shaft proximally. The force placed on the tool shaft by this biasing member accomplishes two functions. First, when the tool is in the static state, the force holds the tool shaft against the actuating component of the steering assembly. In the described version of the invention, these are lever arms 146. This ensures that as soon as there is any displacement of this portion of the steering assembly, the tool shaft 190 is urged distally forward. Secondly, upon the steering assembly returning to the static state, the force imposed by this biasing member urges the tool shaft proximally rearward. This results in the rapid reduction in the tension on the inelastic cable that is holding the tool shaft in the bent position. As discussed above, the reduction of this tension is what causes the tool shaft to return to the unbent state.

In the described version of the invention, the working head 270 has two rotational orientations relative to the tool shaft 190. The invention is not limited to this design. In some versions of the invention, it may be possible to mount the working head 270 to the tool shaft 190 so the head may have any angular orientation around the circle centered on the tool shaft axis. Alternatively, the tool shaft may be mounted to the shell in such a manner that the tool shaft is able to rotate. There are two benefits of these versions of the invention. First this allows the practitioner to set the direction of the bend of the tool shaft relative to the shell 80. Secondly, assuming the angular orientation of the working head 270 is fixed relative to the shell 80, this allows the practitioner to set the angular orientation of the tool shaft relative to the working head.

The number and type of cables may also vary from what has been described. In some versions of the invention, it may be desirable to provide the tool shaft with plural inelastic cables. Likewise there may be constructions of the invention with less than or more than three elastic cables. In some configurations of the invention, the invention may include a single elastic cable. Further, in some versions of the invention, the elastic cables may not be elastic along the whole of their lengths. In these constructions of the invention, an elastic cable may be in the form of an assembly that includes a spring to which one or more sections of inelastic cable are attached. In a version of the invention with a single elastic cable, that cable is often located symmetric relative to the inelastic cable relative to the longitudinal axis of the shaft. In versions of the invention in which the bendable section is formed with links, a flexible sleeve is disposed in contiguous lumen that extends through the links. This sleeve serves to inhibit the lateral movement of the links.

In alternative versions of this invention, all or some of the driver/receiver may be built into the shell and tube shaft of the tube of the invention. Thus, in an alternative shaver constructed according to this invention, the tube shaft may function as the outer tube of the shaving tube assembly. Likewise, in some versions of the invention, the tool may not include a driver/receiver. An example of such a tool is an electrosurgical ablation tool built according to this invention. In some versions of this type of tool, the distal end head of the tube shaft is the active electrode tip of the tool. Flexible wires internal to tool shaft supply the current hat is sourced from the tip. A cable runs from the tool to a control console. The cable supplies the current that sourced from the tip. The on/off state of the tool is controlled by a footswitch also connected to the control console.

A diagnostic tool of this invention may having a working head that is lens through which image of the tissue adjacent the working head is obtained. This lens may be the distal end of a fiber optic cable that extends through the tool shaft. Still another diagnostic tool of this invention may include a biopsy coring device used to obtain a tissue sample.

It should likewise be appreciated that the tool of this invention is not limited to powered tools. The tool of this invention may be some type of manually operated tool. For example one manually operated tool of this invention may have forceps jaws as a working head. Another manually operated tools may have a pair of scissor blades as the working head. With both these tools a cable would run through the tool shaft. The practitioner manually pulls on and releases the cable to set the jaws or head. Alternatively, this invention can be used to provide spot suction or irrigation to a target site within the patient. In these versions of the invention, the shaft is formed with a lumen through which suction is drawn or through which irrigating solution is pumped. In these versions of the invention, the distal open end of the shaft, the end of the shaft located forward of the bendable section, functions as the tool working member. This open end component of the shaft is the tool working member in that it is the component of the tool through which the suction is drawn into the shaft of the fluid discharged from the shaft.

It should similarly be appreciated that not all therapeutic or diagnostic tools integrated into this invention may include some type of actuating member. For example a tool of this invention wherein the tissue working head is a rasp, a file or a curette may not have a member to actuate the working head. With this type of tool the movement of the body and even the bending of the shaft flexible section may serve to move the working head so the head accomplishes the desired task. Since the species of tools do not require an actuating member, the tool does not need to be provided with a lumen or bore for holding the actuating member. Thus, in these versions of the invention one or both of the shaft rigid section and bendable section may be formed from solid components that do not have axial extending voids.

The invention is not limited to assemblies wherein the steering assembly is manually actuated. In some versions of the invention, a servomotor may be a sub-assembly that translates the tool shaft.

Regardless of the means, manual or motor, used to set the position of the tube shaft and, therefore, the curvature of the shaft, a tool of this invention may include an assembly that sets tool shaft position. By extension, this sets the curvature of the tool shaft. For example, a manually controlled version of this invention may include a pawl and ratchet assembly. When the practitioner advances the tool shaft, the pawl and ratchet assembly locks the tool shaft from reacting to the release of the potential energy from the cables that would both straighten the tool shaft and return the shaft to the proximal position. When the procedure is at a point at which it is necessary to straight to the tool shaft, the pawl of this assembly is released. This allows the release of the potential energy stored by the cables. In a motorized version of the invention the gear assembly that translation the rotational moment of the servo motor to motion that translates the tool shaft performs the same function as the pawl and ratchet assembly. In these versions of the invention, it is necessary to drive the motor in the reverse direction to straighten the tool shaft.

This invention is also not limited to an assemblies that, like illustrated version, include a tool shaft with a rigid section that is straight and a bendable section that, when at rest, is also straight. In some versions of this invention, the tool shaft may have a rigid section that is bent or curved. In some versions of the invention, the tool shaft bendable section may be formed so that when the tool is in the static at rest state, this section is curved. Depending on the construction of the tool, to design the tool so that, when the tool shaft is steered, this bend is either increased or decreased.

Likewise in some constructions of the invention the overall length of the shaft head, the rigid section of the shaft distal to the bendable section may be equal to or even greater than the length of the rigid section proximal to the bendable section.

It is also within the scope of this invention that the tool include plural bendable sections. In these versions of the invention, the tool shaft would include a rigid section between longitudinally adjacent bendable sections. As a result of the longitudinal displacement of the tool shaft, each of these bendable sections flexes, curves, from the at rest state of the section.

It should similarly be appreciated that the selectively bendable tool of this invention may have applications outside of the fields of medicine and surgery.

Therefore, it is an object of the appended claims to cover all such variations and modifications that come within the true spirit and scope of the invention.

The invention claimed is:

1. A surgical tool comprising:
a body;
a shaft extending distally from the body and comprising a shaft bendable section, and a working head distal to the shaft bendable section;
a flexible inelastic cable coupled to the body and the shaft;
a flexible elastic cable coupled to the body and the shaft, the flexible elastic cable being arcuately spaced from the flexible inelastic cable; and
a steering assembly coupled to the shaft and configured to cause longitudinal displacement of the shaft relative to the body to tension the flexible inelastic cable and the flexible elastic cable to bend the shaft bendable section in a direction of the flexible inelastic cable.

2. The surgical tool of claim 1, wherein the working head forms an active tip being one of one of an electrosurgical tip configured to emit radiofrequency or thermal energy, and an optical tip configured to emit light energy, and wherein one of the flexible inelastic cable and the flexible elastic cable is configured to supply energy to the active tip.

3. The surgical tool of claim 1, wherein the working head comprises a lens through which an image of adjacent tissue is configured to be imaged, and wherein the surgical tool further comprises a fiber optic cable extending through the shaft and coupled to the lens.

4. The surgical tool of claim 1, wherein the working head comprises a biopsy coring device configured to obtain a tissue sample.

5. The surgical tool of claim 1, wherein the working head comprises forceps jaws or scissor blades, and wherein the surgical tool further comprises an actuator cable extending through the shaft and coupled to the forceps jaws or the scissor blades.

6. The surgical tool of claim 1, wherein the shaft defines a lumen configured to be arranged in fluid communication with a source of suction or irrigation.

7. The surgical tool of claim 1, wherein the working head is one of a rasp, a file, and a curette, and wherein the bending the shaft bendable section in the direction of the flexible inelastic cable is configured to manipulate tissue.

8. The surgical tool of claim 1, wherein the shaft further comprises a shaft rigid section adjacent to the shaft bendable section, and wherein the shaft rigid section is bent or curved.

9. The surgical tool of claim 1, wherein the shaft bendable section is plural shaft bendable sections separated by a shaft rigid section, and wherein the longitudinal displacement of the shaft relative to the body causes each of the plural shaft bendable sections to bend in the direction of the flexible inelastic cable.

10. The surgical tool of claim 1, wherein the shaft defines a lumen and further comprises a plurality of links forming the shaft bendable section, and wherein a flexible sleeve is disposed within the lumen that extends through the plurality of links.

11. The surgical tool of claim 1, further comprising an actuator ring rigidly secured to the shaft proximal to the shaft bendable section, wherein actuation of the steering assembly urges the actuator ring distally to cause longitudinal displacement of the shaft relative to the body.

12. The surgical tool of claim 1, wherein the steering assembly further comprises a manually actuated member.

13. The surgical tool of claim 1, wherein the shaft bendable section is formed by links arranged in series, wherein adjacent links are engaged by tabs disposed in sockets such that the adjacent links are pivotable relative to one another, and wherein the flexible inelastic cable is arcuately spaced from the tabs and the sockets such that angular orientation of the bend is fixed relative to the body of the surgical tool.

14. The surgical tool of claim 1, wherein the shaft defines a lumen, and wherein the surgical tool further comprises:
a cradle; and
a shaver comprising a motor, and a shaver shaft comprising a flexible section configured to be aligned with the shaft bendable section with the motor of the shaver supported on the cradle.

15. A surgical tool comprising:
a body;
a shaft extending distally from the body and comprising a shaft bendable section, and a working head distal to the shaft bendable section and forming an active tip;
a flexible inelastic cable coupled to the body and the shaft; and
a flexible elastic cable coupled to the body and the shaft, the flexible elastic cable being arcuately spaced from the flexible inelastic cable, wherein the flexible inelastic cable and the flexible elastic cable are configured to be placed in tension such that the shaft bendable section bends towards the flexible inelastic cable and the flexible elastic cable longitudinally compresses the shaft bendable section,
wherein one of the flexible inelastic cable and the flexible elastic cable is configured to supply energy to the active tip.

16. The surgical tool of claim 15, wherein the active tip is one of an electrosurgical tip configured to emit radiofrequency or thermal energy, and an optical tip configured to emit light energy.

17. The surgical tool of claim 15, wherein the shaft bendable section is formed by links arranged in series, wherein adjacent links are engaged by tabs disposed in sockets such that the adjacent links are pivotable relative to one another, and wherein the flexible inelastic cable is arcuately spaced from the tabs and the sockets such that angular orientation of the bend is fixed relative to the body of the surgical tool.

18. The surgical tool of claim 15, wherein the shaft is longitudinally movable relative to the body.

19. A surgical tool comprising:
a body comprising a cradle;
a shaft extending distally from the body and defining a lumen, the shaft comprising links arranged in series to form a shaft bendable section;
a flexible inelastic cable coupled to the body and the shaft;
a flexible elastic cable coupled to the body and the shaft, the flexible elastic cable being arcuately spaced from the flexible inelastic cable;
a steering assembly coupled to the shaft and configured to receive an input to tension the flexible inelastic cable and the flexible elastic cable such that the shaft bendable section bends towards the flexible inelastic cable and the flexible elastic cable longitudinally compresses the shaft bendable section; and
a shaver comprising a motor, and a shaver shaft comprising a flexible section configured to be directed through the lumen to be aligned with the shaft bendable section with the motor of the shaver removably supported on the cradle.

20. The surgical tool of claim 19, wherein the body defines notches configured to limit to two rotational orientations by which the shaver may be directed through the lumen of the shaft for the motor to be supported on the cradle.

\* \* \* \* \*